(12) United States Patent
Furusato et al.

(10) Patent No.: US 9,969,935 B2
(45) Date of Patent: *May 15, 2018

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yoshimasa Furusato, Chiba (JP); Masayuki Saito, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 17 days.

This patent is subject to a terminal disclaimer.

(21) Appl. No.: 15/038,739

(22) PCT Filed: Sep. 29, 2014

(86) PCT No.: PCT/JP2014/075834
§ 371 (c)(1),
(2) Date: May 24, 2016

(87) PCT Pub. No.: WO2015/079797
PCT Pub. Date: Apr. 6, 2015

(65) Prior Publication Data
US 2016/0376505 A1      Dec. 29, 2016

(30) Foreign Application Priority Data

Nov. 29, 2013  (JP) ................................ 2013-247063

(51) Int. Cl.
| | |
|---|---|
| *C09K 19/34* | (2006.01) |
| *C09K 19/54* | (2006.01) |
| *C07D 211/12* | (2006.01) |
| *C07D 211/18* | (2006.01) |
| *C07D 211/22* | (2006.01) |
| *C09K 19/12* | (2006.01) |
| *C09K 19/30* | (2006.01) |

(52) U.S. Cl.
CPC ............ *C09K 19/54* (2013.01); *C07D 211/12* (2013.01); *C07D 211/18* (2013.01); *C07D 211/22* (2013.01); *C09K 19/3001* (2013.01); *C09K 19/3066* (2013.01); *C09K 19/3068* (2013.01); *C09K 19/3402* (2013.01); *C09K 19/3483* (2013.01); *C09K 19/542* (2013.01); *C09K 2019/122* (2013.01); *C09K 2019/123* (2013.01); *C09K 2019/301* (2013.01); *C09K 2019/3009* (2013.01); *C09K 2019/3027* (2013.01); *C09K 2019/3037* (2013.01); *C09K 2019/3422* (2013.01); *C09K 2019/3425* (2013.01); *C09K 2019/548* (2013.01)

(58) Field of Classification Search
CPC ..................................................... C09K 19/34
See application file for complete search history.

(56) References Cited

U.S. PATENT DOCUMENTS

| | | |
|---|---|---|
| 4,166,814 A | 9/1979 | Karrer |
| 2003/0127627 A1 | 7/2003 | Amakawa et al. |
| 2007/0108411 A1 | 5/2007 | Saito et al. |

FOREIGN PATENT DOCUMENTS

| | | | |
|---|---|---|---|
| CN | 100497523 | 6/2009 | |
| DE | 102011013007 | * 10/2011 | ......... C09K 19/3001 |
| EP | 1785466 | 5/2007 | |
| JP | 2003-226876 | 8/2003 | |
| JP | 2007-137921 | 6/2007 | |
| TW | 201339282 | 10/2013 | |

OTHER PUBLICATIONS

"International Search Report (Form PCT/ISA/210)", dated Dec. 9, 2014, with English translation thereof, pp. 1-3.
"Office Action of China Counterpart Application," with English translation thereof, dated Jan. 2, 2018, p.1-p.13, in which the listed references (U.S. Pat. No. 1 and foreign patent No. 1-2) were cited.
"Office Action of Taiwan Counterpart Application," with English translation thereof, dated Feb. 9, 2018, p.1-p.13, in which the listed references (foreign patent No. 3) were cited.

* cited by examiner

*Primary Examiner* — Chanceity Robinson
(74) *Attorney, Agent, or Firm* — JCIPRNET

(57) ABSTRACT

The liquid crystal composition contains a compound contributing to high stability to heat or ultraviolet light, has negative dielectric anisotropy and has a nematic phase, and may contain a specific compound having high negative dielectric anisotropy as a first component, a specific compound having a high maximum temperature or small viscosity as a second component, and a specific compound having a polymerizable group.

16 Claims, No Drawings

LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2014/075834, filed on Sep. 29, 2014, which claims the priority benefit of Japan application no. 2013-247063, filed on Nov. 29, 2013. The entirety of each of the above-mentioned patent applications is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having a negative dielectric anisotropy, and a liquid crystal display device including the composition and having such a mode as an IPS mode, a VA mode, an FFS mode and an FPA mode. The invention also relates to a polymer sustained alignment mode liquid crystal display device.

BACKGROUND ART

In a liquid crystal display device, a classification based on an operating mode of liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is further classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving the characteristics of the composition. Table 1 below summarizes a relationship in two characteristics. The characteristics of the composition will be further described based on a commercially available AM device. A temperature range of the nematic phase relates to a temperature range in which the device can be used. A preferred maximum temperature of the nematic phase is about 70° C. or higher and a preferred minimum temperature of the nematic phase is about −10° C. or lower. Viscosity of the composition relates to a response time in the device. A short response time is preferred for displaying moving images on the device. A shorter response time even by one millisecond is desirable. Accordingly, a small viscosity in the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity [1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |

[1] A composition can be injected into a liquid crystal display device in a shorter period of time.

An optical anisotropy of the composition relates to a contrast ratio in the device. In accordance with a mode of the device, a large optical anisotropy or a small optical anisotropy, more specifically, a suitable optical anisotropy is required. A product (Δn×d) of the optical anisotropy (Δn) of the composition and a cell gap (d) in the device is designed so as to maximize the contrast ratio. A suitable value of the product depends on a kind of the operating mode. The suitable value is in the range of about 0.30 micrometer to about 0.40 micrometer in a device having the VA mode, and in the range of about 0.20 micrometer to about 0.30 micrometer in a device having the IPS mode or the FFS mode. In the above cases, a composition having a large optical anisotropy is preferred for a device having a small cell gap. A large dielectric anisotropy in the composition contributes to a low threshold voltage, a small electric power consumption and a large contrast ratio in the device. Therefore, a large dielectric anisotropy is preferred. A large specific resistance in the composition contributes to a large voltage holding ratio and a large contrast ratio in a device. Accordingly, a composition having a large specific resistance at room temperature and also at a high temperature in an initial stage is preferred. A composition having a large specific resistance at room temperature and also at a high temperature even after the device has been used for a long period of time is preferred. Stability of the composition to ultraviolet light and heat relates to a service life of the device. In the case where the stability is high, the device has a long service life. Such characteristics are preferred for an AM device for use in a liquid crystal projector, a liquid crystal television and so forth.

In a polymer sustained alignment (PSA) mode liquid crystal display device, a liquid crystal composition containing a polymer is used. First, a composition to which a small amount of polymerizable compound is added is injected into a device. Next, the composition is irradiated with ultraviolet light while voltage is applied between substrates of the device. The polymerizable compound is polymerized to produce a polymer network structure in the composition. In the composition, alignment of liquid crystal molecules can be controlled, and therefore a response time of the device is shortened and image persistence is reduced. Such an effect of the polymer can be expected for the device having a mode such as a TN mode, an ECB mode, an OCB mode, an IPS mode, a VA mode, an FFS mode or an FPA mode.

A composition having a positive dielectric anisotropy is used for an AM device having the TN mode. A composition having a negative dielectric anisotropy is used for an AM device having the VA mode. A composition having a positive or negative dielectric anisotropy is used for an AM device having the IPS mode or the FFS mode. A composition having a positive or negative dielectric anisotropy is used for a polymer sustained alignment (PSA) mode AM device. Compound (1) in the present application is disclosed in Patent literature No. 1 described below.

CITATION LIST

Patent Literature

Patent literature No. 1: DE 102,011,013,007 A.

SUMMARY OF INVENTION

Technical Problem

One of the aims of the invention is to provide a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another aim is to provide a liquid crystal composition having a suitable balance regarding at least two of the characteristics. A further aim is to provide a liquid crystal display device including such a composition. An additional aim is an AM device having characteristics such as a short response time, a large voltage holding ratio, a low threshold voltage, a large contrast ratio and a long service life.

Solution to Problem

The invention concerns a liquid crystal composition that has a negative dielectric anisotropy and a nematic phase, and contains at least one compound selected from the group of compounds represented by formula (1), and a liquid crystal display device including the composition.

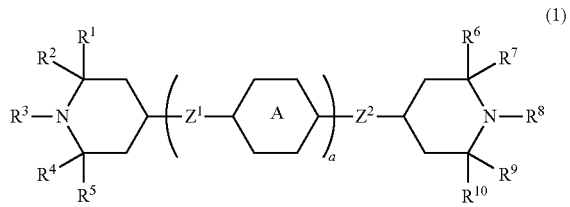

In formula (1), $R^1$, $R^2$, $R^4$, $R^5$, $R^6$, $R^7$, $R^9$ and $R^{10}$ are independently hydrogen or alkyl having 1 to 4 carbons; $R^3$ and $R^8$ are independently hydrogen or alkyl having 1 to 15 carbons; ring A is 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyran-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen; $Z^1$ and $Z^2$ are independently a single bond or alkylene having 1 to 10 carbons, and in the alkylene, at least one piece of —CH$_2$— may be replaced by —O—, at least one piece of —CH$_2$— may be replaced by —CH=CH— and —C≡C—, and in the groups, at least one piece of hydrogen may be replaced by fluorine; and a is 1, 2 or 3.

Advantageous Effects of Invention

An advantage of the invention is a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another advantage is a liquid crystal composition having a suitable balance regarding at least two characteristics. Another advantage is a liquid crystal display device including such a composition. Another advantage is an AM device having characteristics such as a short response time, a large voltage holding ratio, a low threshold voltage, a large contrast ratio and a long service life.

DESCRIPTION OF EMBODIMENTS

Usage of terms herein is as described below. "Liquid crystal composition" and "liquid crystal display device" may be occasionally abbreviated as "composition" and "device," respectively. The liquid crystal display device is a generic term for a liquid crystal display panel and a liquid crystal display module. The liquid crystal compound is a generic term for a compound having a liquid crystal phase such as a nematic phase and a smectic phase and a compound having no liquid crystal phase but being mixed with the composition for the purpose of adjusting characteristics such as a temperature range of the nematic phase, viscosity and dielectric anisotropy. The compound has a six-membered ring such as 1,4-cyclohexylene or 1,4-phenylene, and a rod like molecular structure. A polymerizable compound is a compound added for the purpose of producing a polymer in the composition.

The liquid crystal composition is prepared by mixing two or more liquid crystal compounds. A proportion (content) of the liquid crystal compound is expressed in terms of weight percent (% by weight) based on the weight of the liquid crystal composition. An additive such as an optically active compound, an antioxidant, an ultraviolet light absorbent, a dye, a defoaming agent, a polymerizable compound, a polymerization initiator and a polymerization inhibitor is added to the composition when necessary. A proportion (amount of addition) of the additive is expressed in terms of weight percent (% by weight) based on the weight of the liquid crystal composition in a manner similar to the proportion of the liquid crystal compound. Weight parts per million (ppm) may also be used. A proportion of the polymerization initiator and the polymerization inhibitor is exceptionally expressed based on the weight of the polymerizable compound.

"Maximum temperature of the nematic phase" may be occasionally abbreviated as "maximum temperature." "Minimum temperature of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and that the composition has a large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in an initial stage, and that the device has a large voltage holding ratio at room temperature and also at a temperature close to the maximum temperature of the nematic phase even after the device has been used for a long period of time. An expression "increase dielectric anisotropy" means that the value positively increases when the composition has a positive dielectric anisotropy, and means that the value negatively increases when the composition has a negative dielectric anisotropy.

An expression "at least one piece of 'A' may be replaced by 'B'" means that the number of 'A' is arbitrary. When the number of 'A' is one, a position of 'A' is arbitrary, and also when the number of 'A' is two or more, the positions can be selected without restriction. A same rule also applies to an expression "at least one piece of 'A' is replaced by 'B'."

In formula (1) to formula (4), a symbol A, B, C or the like surrounded by a hexagonal shape corresponds to ring A, ring B, ring C or the like, respectively. In formula (4), an oblique line crossing the hexagonal shape of ring G means that a bonding position on a ring can be arbitrarily selected for the $P^1$-$Sp^1$ group. A same rule also applies to a $P^2$-$Sp^2$ group of ring I or the like. A subscript such as f represents the number of the groups to be bonded with ring G or the like. When f is 2, two groups exist on ring G. Two groups represented by $P^1$-$Sp^1$ may be identical or different. A same rule also applies to arbitrary two when f is larger than 2. A same rule also applies to any other group. A compound represented by formula (1) may be occasionally abbreviated as compound (1). The abbreviation may also apply to a compound represented by formula (2) or the like. Compound (1) means one compound or two or more compounds represented by formula (1). A symbol of terminal group $R^{11}$ is used for a plurality of compounds in chemical formulas of component compounds. In the compounds, two groups represented by two of arbitrary pieces of $R^{11}$ may be identical or different. In one case, for example, $R^1$ of compound (2-1) is ethyl and $R^{11}$ of compound (2-2) is ethyl. In another case, $R^{11}$ of compound (2-1) is ethyl and $R^{11}$ of compound (2-2) is propyl. A same rule also applies to a symbol of other end groups or the like. In formula (1), when a is 2, two rings A exist. In the compounds, two rings represented by two rings A may be identical or different. A same rule also applies to two of arbitrary rings A when a is larger than 2. A same rule also applies to a symbol $Z^3$, ring B or the like.

Then, 2-fluoro-1,4-phenylene means two divalent groups described below. In the chemical formula, fluorine may be leftward (L) or rightward (R). A same rule also applies to an asymmetrical divalent group ring such as tetrahydropyran-2,5-diyl.

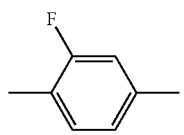
(L)

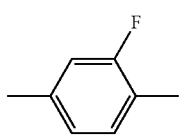
(R)

The invention includes the items described below.

Item 1. A liquid crystal composition that has a negative dielectric anisotropy and a nematic phase, and contains at least one compound selected from the group of compounds represented by formula (1):

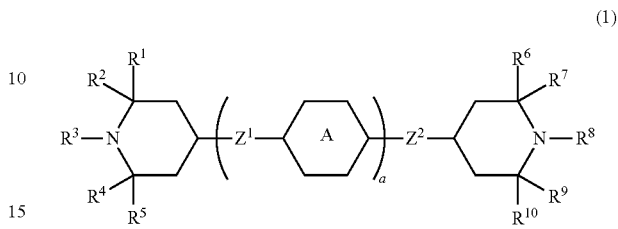

(1)

wherein, in formula (1), $R^1$, $R^2$, $R^4$, $R^5$, $R^6$, $R^7$, $R^9$ and $R^{10}$ are independently hydrogen or alkyl having 1 to 4 carbons; $R^3$ and $R^8$ are independently hydrogen or alkyl having 1 to 15 carbons; ring A is 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyran-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen; $Z^1$ and $Z^2$ are independently a single bond or alkylene having 1 to 10 carbons, and in the alkylene, at least one piece of —CH$_2$— may be replaced by —O—, at least one piece of —CH$_2$—CH$_2$— may be replaced by —CH=CH— or —C≡C—, and in the groups, at least one piece of hydrogen may be replaced by fluorine; and a is 1, 2 or 3.

Item 2. The liquid crystal composition according to item 1, containing at least one compound selected from the group of compounds represented by formula (1-1) to formula (1-3):

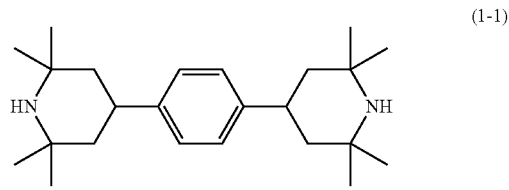
(1-1)

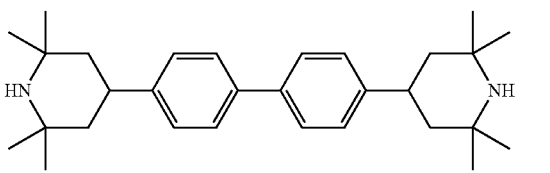
(1-2)

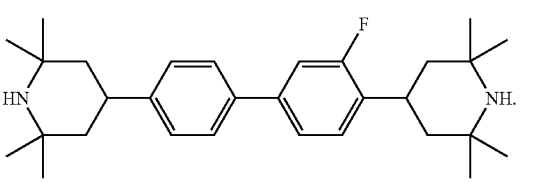
(1-3)

Item 3. The liquid crystal composition according to item 1, wherein a proportion of a compound represented by formula (1) is in the range of 0.005% by weight to 1% by weight based on the weight of the liquid crystal composition.

Item 4. The liquid crystal composition according to any one of items 1 to 3, containing at least one compound selected from the group of compounds represented by formula (2) as a first component:

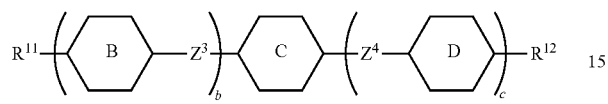
(2)

wherein, in formula (2), $R^{11}$ and $R^{12}$ are independently alkyl having 1 to 12 carbons, alkoxy having 1 to 12 carbons, alkenyl having 2 to 12 carbons or alkenyloxy having 2 to 12 carbons; ring B and ring D are independently 1, 4-cyclohexylene, 1,4-cyclohexenylene, 1,4-phenylene, 1,4-phenylene in which at least one piece of hydrogen is replaced by fluorine or chlorine, or tetrahydropyran-2,5-diyl; ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7, 8-difluorochroman-2,6-diyl; $Z^3$ and $Z^4$ are independently a single bond, ethylene, methyleneoxy or carbonyloxy; b is 1, 2 or 3 and c is 0 or 1; and a sum of b and c is 3 or less.

Item 5. The liquid crystal composition according to any one of items 1 to 4, containing at least one compound selected from the group of compounds represented by formula (2-1) to formula (2-19) as the first component:

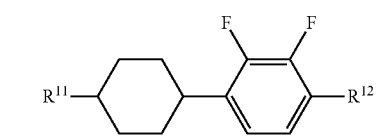
(2-1)

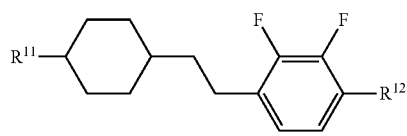
(2-2)

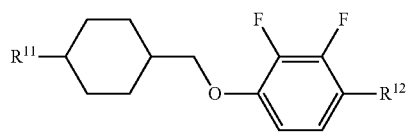
(2-3)

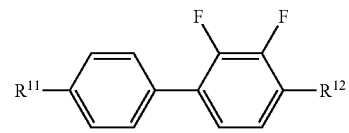
(2-4)

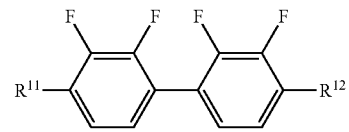
(2-5)

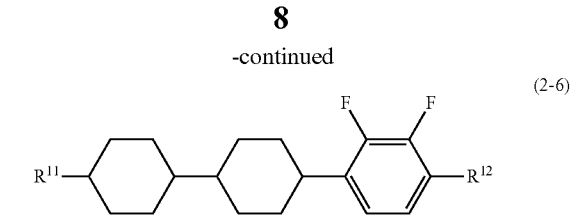
(2-6)

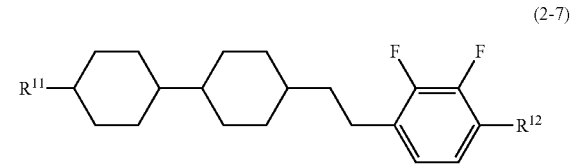
(2-7)

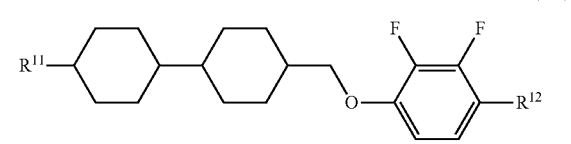
(2-8)

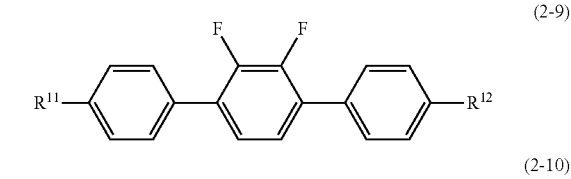
(2-9)

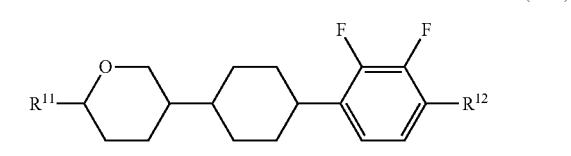
(2-10)

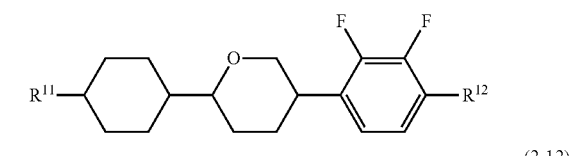
(2-11)

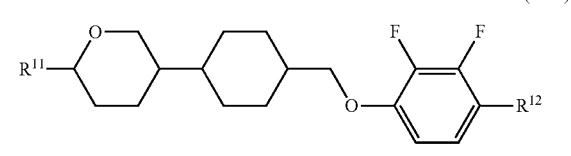
(2-12)

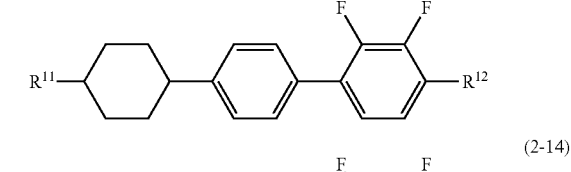
(2-13)

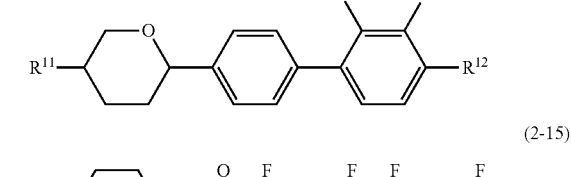
(2-14)

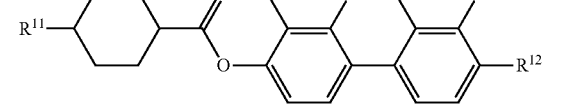
(2-15)

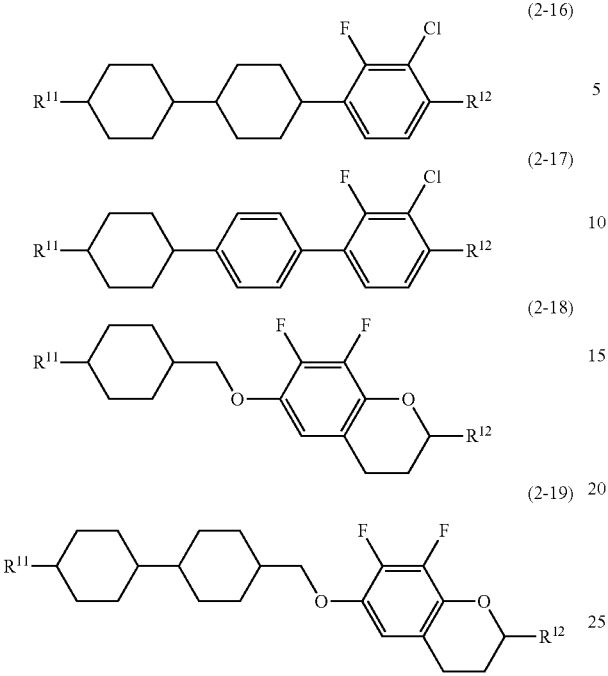

wherein, in formula (2-1) to formula (2-19), $R^{11}$ and $R^{12}$ are independently alkyl having 1 to 12 carbons, alkoxy having 1 to 12 carbons, alkenyl having 2 to 12 carbons or alkenyloxy having 2 to 12 carbons.

Item 6. The liquid crystal composition according to item 4 or 5, wherein a proportion of the first component is in the range of 10% by weight to 90% by weight based on the weight of the liquid crystal composition.

Item 7. The liquid crystal composition according to any one of items 1 to 6, containing at least one compound selected from the group of compounds represented by formula (3) as a second component:

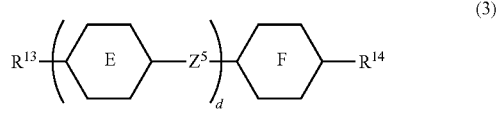

wherein, in formula (3), $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one piece of hydrogen is replaced by fluorine; ring E and ring F are independently 1,4-cyclohexylene, 1,4-phenylene, 2-fluoro-1,4-phenylene or 2,5-difluoro-1,4-phenylene; $Z^5$ is a single bond, ethylene or carbonyloxy; and d is 1, 2 or 3.

Item 8. The liquid crystal composition according to any one of items 1 to 7, containing at least one compound selected from the group of compounds represented by formula (3-1) to formula (3-13) as the second component:

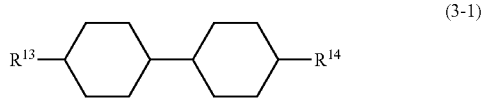

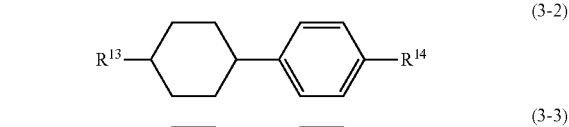

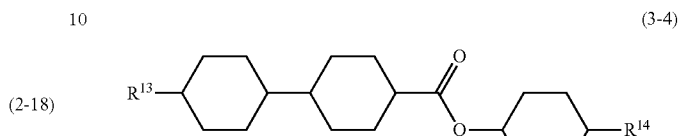

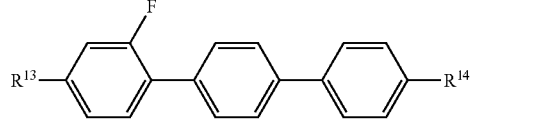

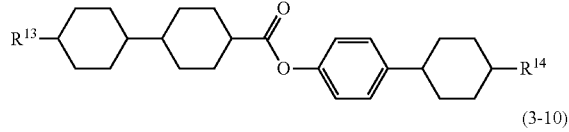

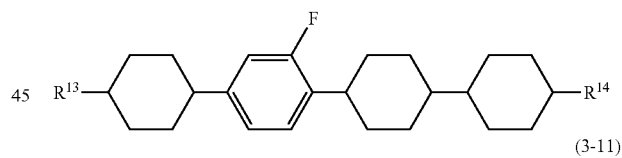

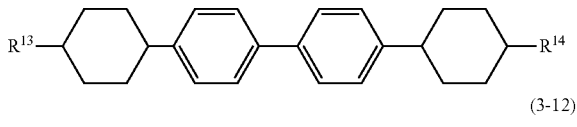

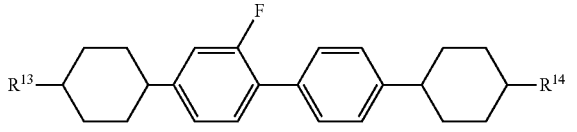

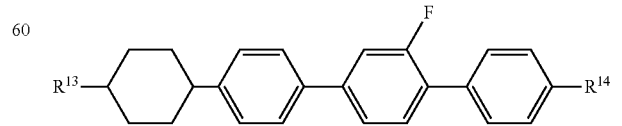

wherein, in formula (3-1) to formula (3-13), $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one piece of hydrogen is replaced by fluorine.

Item 9. The liquid crystal composition according to item 7 or 8, wherein a proportion of the second component is in the range of 10% by weight to 90% by weight based on the weight of the liquid crystal composition.

Item 10. The liquid crystal composition according to any one of items 1 to 9, containing at least one polymerizable compound selected from the group of compounds represented by formula (4):

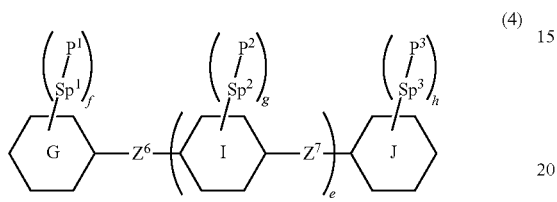

(4)

wherein, in formula (4), ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen; ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen; $Z^6$ and $Z^7$ are independently a single bond or alkylene having 1 to 10 carbons, and in the alkylene, at least one piece of —CH$_2$— may be replaced by —O—, —CO—, —COO— or —OCO—, at least one piece of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one piece of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one piece of —CH$_2$— may be replaced by —O—, —COO—, —OCO— or —OCOO—, at least one piece of —CH$_2$—CH$_2$— may be replaced by —CH=CH— or —C≡C—, and in the groups, at least one piece of hydrogen may be replaced by fluorine or chlorine; e is 0, 1 or 2; f, g and h are independently 0, 1, 2, 3 or 4; and a sum of f, g and h is 1 or more.

Item 11. The liquid crystal composition according to item 10, wherein, in formula (4) described in item 10, $P^1$, $P^2$ and $P^3$ are independently a polymerizable group selected from the group of groups represented by formula (P-1) to formula (P-6):

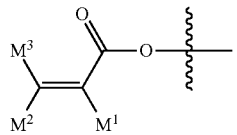

(P-1)

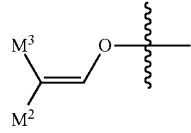

(P-2)

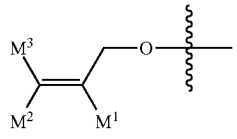

(P-3)

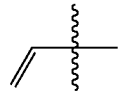

(P-4)

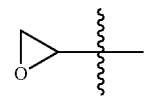

(P-5)

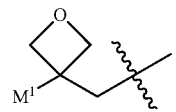

(P-6)

wherein, in formula (P-1) to formula (P-6), $M^1$, $M^2$ and $M^3$ are independently hydrogen, fluorine, alkyl having 1 to 5 carbons, or alkyl having 1 to 5 carbons in which at least one piece of hydrogen is replaced by halogen; and when both of $P^1$ and $P^3$ are a group represented by formula (P-4), at least one of $Sp^1$ and $Sp^3$ is alkylene in which at least one piece of —CH$_2$— is replaced by —O—, —COO—, —OCO— or —OCOO—.

Item 12. The liquid crystal composition according to any one of items 1 to 11, containing at least one polymerizable compound selected from the group of compounds represented by formula (4-1) to formula (4-27):

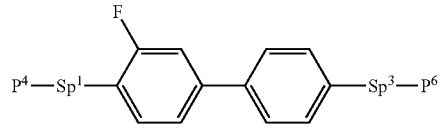

(4-1)

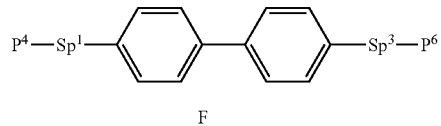

(4-2)

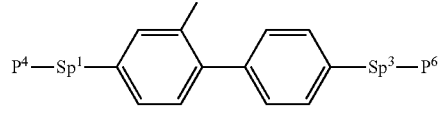

(4-3)

(4-4) 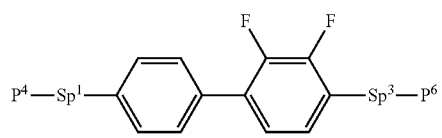
(4-5) 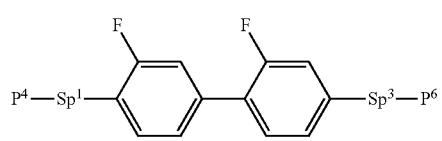
(4-6) 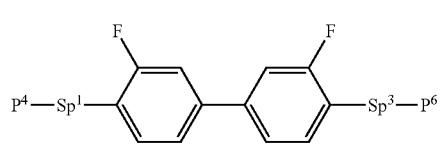
(4-7) 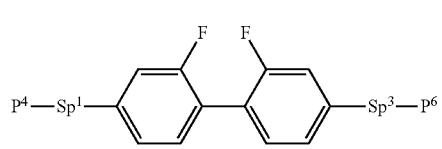
(4-8) 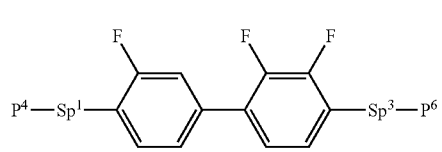
(4-9) 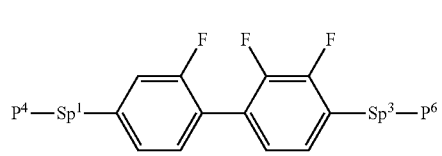
(4-10) 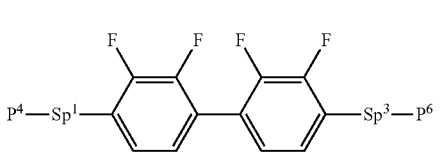
(4-11) 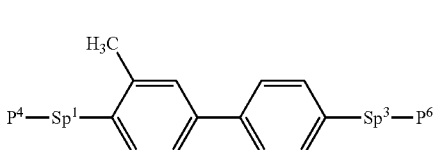
(4-12) 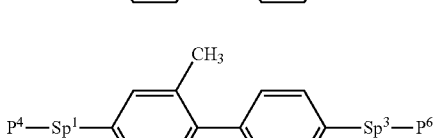
(4-13) 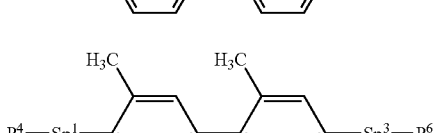
(4-14) 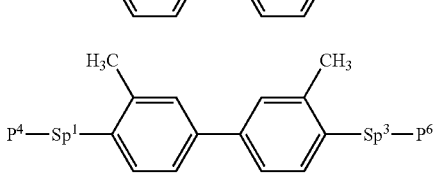
(4-15) 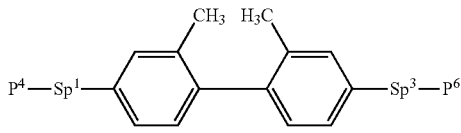
(4-16) 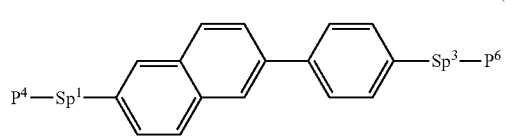
(4-17) 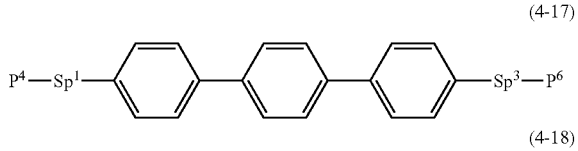
(4-18) 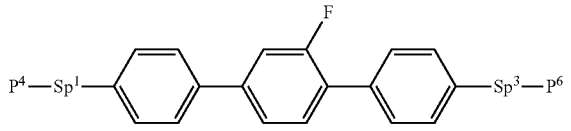
(4-19) 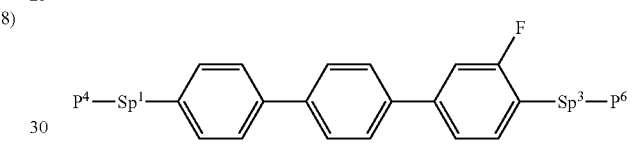
(4-20) 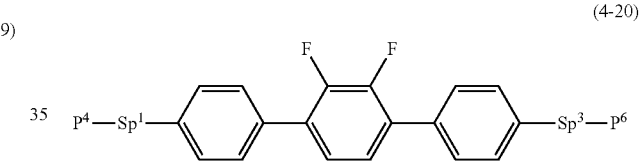
(4-21) 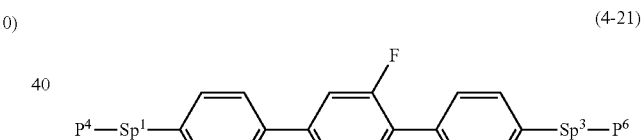
(4-22) 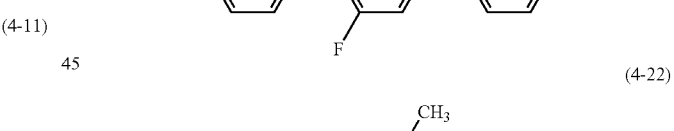
(4-23) 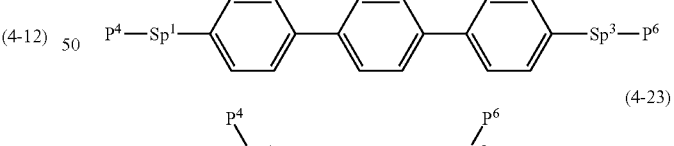
(4-24) 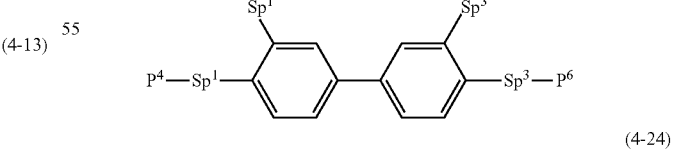
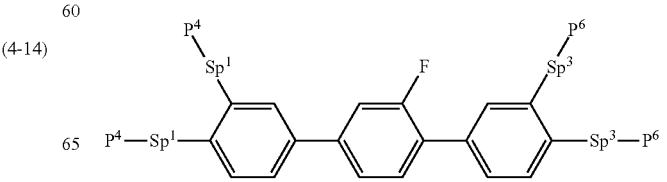

(4-25)

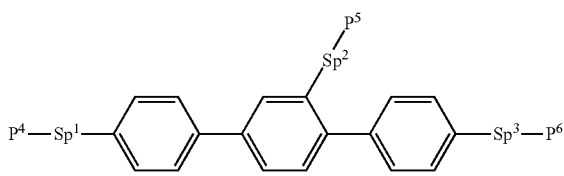

(4-26)

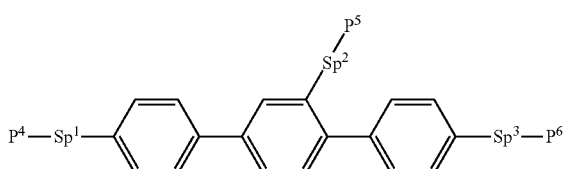

(4-27)

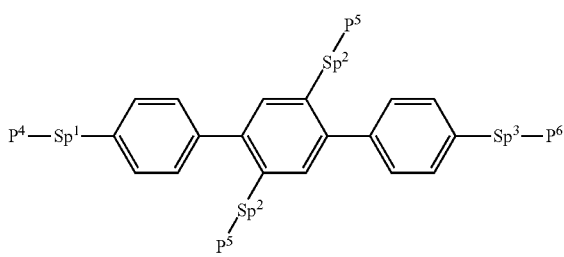

wherein, in formula (4-1) to formula (4-27), $P^4$, $P^5$ and $P^6$ are independently a polymerizable group selected from the group of groups represented by formula (P-1) to formula (P-3);

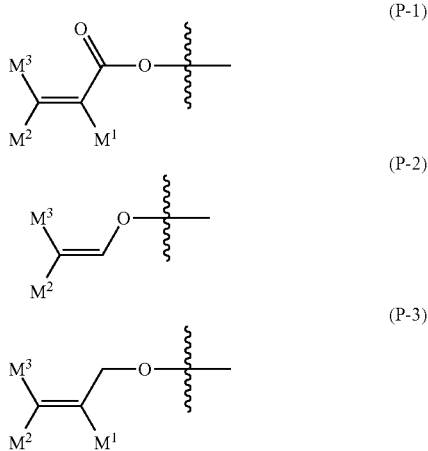

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one piece of hydrogen is replaced by halogen; $Sp^1$, $Sp^2$ and $Sp^3$ are independently a single bond or alkylene having 1 to 10 carbons, and in the alkylene, at least one piece of —CH$_2$— may be replaced by —O—, —COO—, —OCO— or —OCOO—, at least one piece of —CH$_2$—CH$_2$— may be replaced by —CH═CH— or —C≡C—, and in the groups, at least one piece of hydrogen may be replaced by fluorine or chlorine.

Item 13. The liquid crystal composition according to item 10, wherein a proportion of a compound represented by formula (4) is in the range of 0.03% by weight to 10% by weight based on the weight of the liquid crystal composition.

Item 14. A liquid crystal display device including the liquid crystal composition according to any one of items 1 to 13.

Item 15. The liquid crystal display device according to item 14, wherein an operating mode in the liquid crystal display device is an IPS mode, a VA mode, an FFS mode or an FPA mode, and a driving mode in the liquid crystal display device is an active matrix mode.

Item 16. A polymer sustained alignment mode liquid crystal display device, wherein the device includes the liquid crystal composition according to any one of items 10 to 13, and the polymerizable compound in the liquid crystal composition is polymerized.

Item 17. Use of the liquid crystal composition according to any one of items 1 to 13 in a liquid crystal display device.

Item 18. Use of the liquid crystal composition according to any one of items 10 to 13 in a polymer sustained alignment mode liquid crystal display device.

The invention further includes the following items: (a) the composition, further containing at least one additive such as an optically active compound, an antioxidant, an ultraviolet light absorbent, a dye, a defoaming agent, a polymerizable compound, a polymerization initiator and a polymerization inhibitor; (b) an AM device, including the composition; (c) a polymer sustained alignment (PSA) mode AM device, further including a composition containing the polymerizable compound; (d) the polymer sustained alignment (PSA) mode AM device, wherein the device includes the composition, and the polymerizable compound in the composition is polymerized; (e) a device that includes the composition and has a PC mode, a TN mode, an STN mode, an ECB mode, an OCB mode, an IPS mode, a VA mode, an FFS mode or an FPA mode; (f) a transmission device, including the composition; (g) use of the composition as a composition having a nematic phase; and (h) use of the composition as an optically active composition by adding an optically active compound.

The composition of the invention will be described in the following order. First, a constitution of the component compounds in the composition will be described. Second, main characteristics of the component compounds and main effects of the compounds on the composition will be described. Third, a combination of components in the composition, a preferred proportion of the component compounds and the basis thereof will be described. Fourth, a preferred embodiment of the component compounds will be described. Fifth, a preferred component compound will be shown. Sixth, an additive that may be added to the composition will be described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, the additive or the like in addition to the compounds selected from compound (1), compound (2), compound (3) and compound (4). "Any other liquid crystal compound" means a liquid crystal compound different from compound (2) and compound (3). Such a compound is mixed with the composition for the purpose of further adjusting the characteristics. The additive includes the optically active compound, the antioxidant, the ultraviolet light absorbent, the dye, the defoaming agent, the polymerizable compound, the polymerization initiator and the polymerization inhibitor.

Composition B consists essentially of compounds selected from the group of compound (1), compound (2), compound (3) and compound (4). A term "essentially" means that the composition may contain the additive, but does not contain any other liquid crystal compound. Composition B has a smaller number of components than composition A has. Composition B is preferred to composition A in view of cost reduction. Composition A is preferred to composition B in view of possibility of further adjusting characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium," and a symbol S stands for "small" or "low." The symbols L, M and S represent a classification based on a qualitative comparison among the component compounds, and 0 (zero) means "a value is zero or close to zero."

TABLE 2

Characteristics of Compounds

| Compounds | Compound (2) | Compound (3) |
|---|---|---|
| Maximum temperature | S to M | S to L |
| Viscosity | L | S to M |
| Optical anisotropy | M to L | S to L |
| Dielectric anisotropy | L [1)] | 0 |
| Specific resistance | L | L |

[1)] A value of the dielectric anisotropy is negative, and the symbol shows magnitude of an absolute value.

Upon mixing the component compounds with the composition, the main effects of the component compounds on the characteristics of the composition are as described below. Compound (1) contributes to a high stability to heat or ultraviolet light. Compound (1) produces no difference in maximum temperature, optical anisotropy and dielectric anisotropy characteristics. Compound (2) being the first component increases the dielectric anisotropy and decreases the minimum temperature. Compound (3) being the second component decreases the viscosity or increases the maximum temperature. Compound (4) gives a polymer by polymerization, and the polymer shortens a response time of the device and improves image persistence.

Third, the combination of the components in the composition, the preferred proportion of the component compounds and the basis thereof will be described. A preferred combination of components in the composition includes a combination of compound (1) and the first component, a combination of compound (1) and the second component, a combination of compound (1), the first component and the second component, a combination of compound (1), the first component and compound (4), a combination of compound (1), the second component and compound (4), or a combination of compound (1), the first component, the second component and compound (4). A further preferred combination includes a combination of compound (1), the first component and the second component.

A preferred proportion of addition of compound (1) is about 0.005% by weight or more based thereon for contributing to a high stability to heat or ultraviolet light, and about 1% by weight or less based thereon for decreasing the minimum temperature. A further preferred proportion is in the range of about 0.01% by weight to about 0.5% by weight based thereon. A particularly preferred proportion of addition is in the range of about 0.03% by weight to about 0.3% by weight based thereon.

A preferred proportion of the first component is about 10% by weight or more based thereon for increasing the dielectric anisotropy, and about 90% by weight or less for decreasing the minimum temperature. A further preferred proportion is in the range of about 20% by weight to about 80% by weight based thereon. A particularly preferred proportion is in the range of about 30% by weight to about 70% by weight based thereon.

A preferred proportion of the second component is about 10% by weight or more based thereon for increasing the maximum temperature or decreasing the viscosity, and about 90% or less for increasing the dielectric anisotropy. A further preferred proportion is in the range of about 20% by weight to about 80% by weight based thereon. A particularly preferred proportion is in the range of about 30% by weight to about 70% by weight based thereon.

Compound (4) is added to the composition for the purpose of adapting to the polymer sustained alignment mode device. A preferred proportion of addition of the additive is about 0.03% by weight or more for aligning liquid crystal molecules, and about 10% by weight or less for preventing a poor display of the device, based on the weight of the liquid crystal composition. A further preferred proportion of addition is in the range of about 0.1% by weight to about 2% by weight based thereon. A particularly preferred proportion of addition is in the range of about 0.2% by weight to about 1.0% by weight based thereon.

Fourth, the preferred embodiment of the component compounds will be described. In formula (1), $R^1$, $R^2$, $R^4$, $R^5$, $R^6$, $R^7$, $R^9$ and $R^{10}$ are independently hydrogen or alkyl having 1 to 4 carbons. Preferred $R^1$, $R^2$, $R^4$, $R^5$, $R^6$, $R^7$, $R^9$ or $R^{10}$ is hydrogen or methyl. $R^3$ and $R^8$ are independently hydrogen or alkyl having 1 to 15 carbons. Preferred $R^3$ or $R^8$ is hydrogen or methyl.

Ring A is 1,4-cyclohexylene, 1,4-cyclohexenylene, 1,2-phenylene, 1,3-phenylene, 1,4-phenylene, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, decahydronaphthalene-2,6-diyl, dihydropyran-2,5-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 5 carbons, alkoxy having 1 to 5 carbons, or alkyl having 1 to 5 carbons in which at least one piece of hydrogen is replaced by halogen. Preferred ring A is 1,4-cyclohexylene, 1,4-phenylene, 1,4-phenylene in which at least one piece of hydrogen is replaced by fluorine or chlorine, 2-methyl-1,4-phenylene or naphthalene-2,6-diyl. Then, 1,4-cyclohexylene has cis and trans configurations. From a viewpoint of a high maximum temperature, the trans configuration is preferred. Further preferred ring A is 1,4-cyclohexylene, 1,4-phenylene or 2-fluoro-1,4-phenylene. Particularly preferred ring A is 1,4-phenylene or 2-fluoro-1,4-phenylene.

$Z^1$ and $Z^2$ are independently a single bond or alkylene having 1 to 10 carbons, and in the alkylene, at least one piece of —$CH_2$— may be replaced by —O—, at least one piece of —$CH_2$—$CH_2$— may be replaced by —CH=CH— or —C≡C—, and in the groups, at least one piece of hydrogen may be replaced by fluorine. In the groups, at least one piece of hydrogen may be replaced by fluorine. Preferred $Z^1$ or $Z^2$ is a single bond, alkylene having 1 to 5 carbons, —OCH$_2$— or —CH$_2$O—. Further preferred $Z^1$ or $Z^2$ is a single bond.

Then, a is 1, 2 or 3. Preferred a is 1 or 2.

In formula (2) and formula (3), $R^{11}$ and $R^{12}$ are independently alkyl having 1 to 12 carbons, alkoxy having 1 to 12 carbons, alkenyl having 2 to 12 carbons or alkenyloxy having 2 to 12 carbons. Preferred $R^{11}$ or $R^{12}$ is alkyl having 1 to 12 carbons for increasing the stability, or alkoxy having 1 to 12 carbons for increasing the dielectric anisotropy. $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one piece of hydrogen is replaced by fluorine. Preferred $R^{13}$ or $R^{14}$ is alkenyl having 2 to 12 carbons for decreasing the viscosity, or alkyl having 1 to 12 carbons for increasing the stability.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH=CH— in the alkenyl depends on a position of a double bond. Trans is preferred in the alkenyl such as 1-propenyl, 1-butenyl, 1-pentenyl, 1-hexenyl, 3-pentenyl and 3-hexenyl for decreasing the viscosity, for instance. Cis is preferred in the alkenyl such as 2-butenyl, 2-pentenyl and 2-hexenyl. In the alkenyl, straight-chain alkenyl is preferred to branched-chain alkenyl.

Preferred alkenyloxy is vinyloxy, allyloxy, 3-butenyloxy, 3-pentenyloxy or 4-pentenyloxy. Further preferred alkenyloxy is allyloxy or 3-butenyloxy for decreasing the viscosity.

Preferred examples of alkenyl in which at least one piece of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl, for decreasing the viscosity.

Ring B and ring D are independently 1,4-cyclohexylene, 1,4-cyclohexenylene, 1,4-phenylene, 1,4-phenylene in which at least one piece of hydrogen is replaced by fluorine or chlorine, or tetrahydropyran-2,5-diyl. Preferred examples of 1,4-phenylene in which at least one piece of hydrogen is replaced by fluorine or chlorine include 2-fluoro-1,4-phenylene, 2,3-difluoro-1,4-phenylene or 2-chloro-3-fluoro-1,4-phenylene. Preferred ring B or ring D is 1,4-cyclohexylene for decreasing the viscosity, tetrahydropyran-2,5-diyl for increasing the dielectric anisotropy, or 1,4-phenylene for increasing the optical anisotropy. With regard to a configuration of 1,4-cyclohexylene, trans is preferred to cis for increasing the maximum temperature. Tetrahydropyran-2,5-diyl includes:

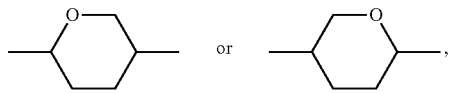 or 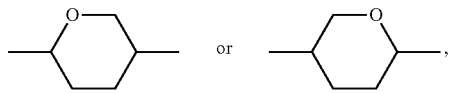, and preferably

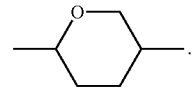.

Ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring C is 2,3-difluoro-1,4-phenylene for decreasing the viscosity, 2-chloro-3-fluoro-1,4-phenylene for decreasing the optical anisotropy, or 7,8-difluorochroman-2,6-diyl for increasing the dielectric anisotropy.

Ring E and ring F are independently 1,4-cyclohexylene, 1,4-phenylene, 2-fluoro-1,4-phenylene or 2,5-difluoro-1,4-phenylene. Preferred ring E or ring F is 1,4-cyclohexylene for decreasing the viscosity or increasing the maximum temperature, or 1,4-phenylene for decreasing the minimum temperature.

$Z^3$ and $Z^4$ are independently a single bond, ethylene, methyleneoxy or carbonyloxy. Preferred $Z^3$ or $Z^4$ is a single bond for decreasing the viscosity, ethylene for decreasing the minimum temperature, or methyleneoxy for increasing the dielectric anisotropy. $Z^5$ is a single bond, ethylene or carbonyloxy. Preferred $Z^5$ is a single bond for decreasing the viscosity.

Then, b is 1, 2 or 3. Preferred b is 1 for decreasing the viscosity, and 2 or 3 for increasing the maximum temperature. Then, c is 0 or 1. Preferred c is 0 for decreasing the viscosity, or 1 for decreasing the minimum temperature. Further, d is 1, 2 or 3. Preferred d is 1 for decreasing the viscosity, or 2 or 3 for increasing the maximum temperature.

In formula (4) and formula (4-1) to formula (4-27), $Sp^1$, $Sp^2$ and $Sp^3$ are independently a single bond or alkylene having 1 to 10 carbons, and in the alkylene, at least one piece of —CH$_2$— may be replaced by —O—, —COO—, —OCO— or —OCOO—, at least one piece of —CH$_2$—CH$_2$— may be replaced by —CH=CH— or —C≡C—, and in the groups, at least one piece of hydrogen may be replaced by fluorine or chlorine. Preferred $Sp^1$, $Sp^2$ or $Sp^3$ is a single bond.

In formula (4), $P^1$, $P^2$ and $P^3$ are independently a polymerizable group. Preferred $P^1$, $P^2$ or $P^3$ is a polymerizable group selected from the group of groups represented by formula (P-1) to formula (P-6). Further preferred $P^1$, $P^2$ or $P^3$ is group (P-1) or group (P-2). Particularly preferred group (P-1) is —OCO—CH=CH$_2$ or —OCO—C(CH$_3$)=CH$_2$. A wavy line of group (P-1) to group (P-6) each represents a part in which a bonding is formed.

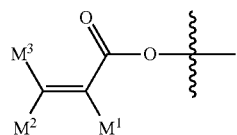 (P-1)

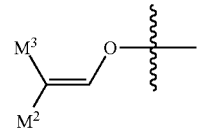 (P-2)

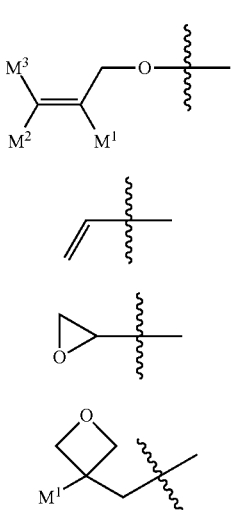

(P-3)

(P-4)

(P-5)

(P-6)

When all of f pieces of $P^1$, g pieces of $P^2$ and h pieces of $P^3$ are group (P-1), $M^1$ (or $M^2$ or $M^3$) of $P^1$, $M^1$ of $P^2$, or $M^1$ of $P^3$ may be identical or different. In group (P-1) to group (P-6), $M^1$, $M^2$ and $M^3$ are independently hydrogen, fluorine, alkyl having 1 to 5 carbons, or alkyl having 1 to 5 carbons in which at least one piece of hydrogen is replaced by halogen. Preferred $M^1$, $M^2$ or $M^3$ is hydrogen or methyl for increasing reactivity. Further preferred $M^1$ is methyl and further preferred $M^2$ or $M^3$ is hydrogen.

When all of f pieces of $P^1$ and h pieces of $P^3$ are group (P-4), at least one of f pieces of $Sp^1$ and h pieces of $Sp^3$ are alkylene in which at least one piece of —CH$_2$— is replaced by —O—, —COO—, —OCO— or —OCOO—. More specifically, a case where all of f pieces of $P^1$ and h pieces of $P^3$ are alkenyl such as 1-propenyl is excluded.

In formula (4-1) to formula (4-27), $P^4$, $P^5$ and $P^6$ are independently groups represented by formula (P-1) to formula (P-3). Preferred $P^4$, $P^5$ or $P^6$ is group (P-1) or group (P-2). Further preferred group (P-1) is —OCO—CH═CH$_2$ or —OCO—C(CH$_3$)═CH$_2$. A wavy line of group (P-1) to group (P-3) each represents a part in which a bonding is formed.

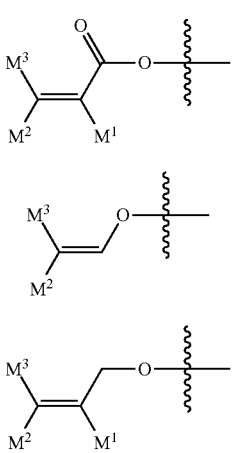

(P-1)

(P-2)

(P-3)

When all of one or two pieces of $P^4$, one or two pieces of $P^5$ and one or two pieces of $P^6$ are group (P-1), $M^1$ (or $M^2$ or $M^3$) of $P^4$, $M^1$ of $P^5$, or $M^1$ of $P^6$ may be identical or different.

In formula (4), ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Preferred ring G or ring J is phenyl. Ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Particularly preferred ring I is 1,4-phenylene or 2-fluoro-1,4-phenylene.

$Z^6$ and $Z^7$ are independently a single bond or alkylene having 1 to 10 carbons, and in the alkylene, at least one piece of —CH$_2$— may be replaced by —O—, —CO—, —COO— or —OCO—, at least one piece of —CH$_2$—CH$_2$— may be replaced by —CH═CH—, —C(CH$_3$)═CH—, —CH═C(CH$_3$)— or —C(CH$_3$)═C(CH$_3$)—, and in the groups, at least one piece of hydrogen may be replaced by fluorine or chlorine. Preferred $Z^6$ or $Z^7$ is a single bond, —CH$_2$CH$_2$—, —CH$_2$O—, —OCH$_2$—, —COO— or —OCO—. Further preferred $Z^6$ or $Z^7$ is a single bond.

Then, e is 0, 1 or 2. Preferred e is 0 or 1. Further, f, g and h are independently 0, 1, 2, 3 or 4, and a sum of f, g and h is 1 or more. Preferred f, g or h is 1 or 2.

Fifth, the preferred component compound is shown. Preferred compound (1) includes compound (1-1) to compound (1-3) described in item 2. Further preferred compound (1) includes compound (1-1) and compound (1-3).

Preferred compound (2) includes compound (2-1) to compound (2-19) described in item 5. In the compounds, at least one first component preferably includes compound (2-1), compound (2-3), compound (2-4), compound (2-6), compound (2-8) or compound (2-13). At least two of the first components preferably includes a combination of compound (2-1) and compound (2-6), a combination of compound (2-1) and compound (2-13), a combination of compound (2-3) and compound (2-6), a combination of compound (2-3) and compound (2-13), or a combination of compound (2-4) and compound (2-8).

Preferred compound (3) includes compound (3-1) to compound (3-13) described in item 8. In the compounds, at least one second component preferably includes compound (3-1), compound (3-3), compound (3-5), compound (3-6), compound (3-7) or compound (3-8). At least two of the second components preferably includes a combination of compound (3-1) and compound (3-3), a combination of compound (3-1) and compound (3-5), or a combination of compound (3-1) and compound (3-6).

Preferred compound (4) includes compound (4-1) to compound (4-27) described in item 12. In the compounds, at least one additive component preferably includes compound (4-1), compound (4-2), compound (4-24), compound (4-25), compound (4-26) or a compound (4-27). At least two of the additive components preferably includes a combination of compound (4-1) and compound (4-2), a combination of compound (4-1) and compound (4-18), a combination of compound (4-2) and compound (4-24), a combination of compound (4-2) and compound (4-25), a combination of compound (4-2) and compound (4-26), a combination of compound (4-25) and compound (4-26), or a combination of compound (4-18) and compound (4-24). In group (P-1) to group (P-3), preferred $M^1$, $M^2$ or $M^3$ includes hydrogen or methyl. Preferred $Sp^1$, $Sp^2$ or $Sp^3$ includes a single bond, —$CH_2CH_2$—, —$CH_2O$—, —$OCH_2$—, —COO—, —OCO—, —CO—CH=CH— or —CH=CH—CO—.

Sixth, the additive that may be added to the composition will be described. Such additives include the optically active compound, the antioxidant, the ultraviolet ray absorbent, the dye, the defoaming agent, the polymerizable compound, the polymerization initiator, the polymerization inhibitor and so forth. The optically active compound is added to the composition for the purpose of inducing a helical structure in liquid crystals to give a twist angle. Examples of such a compound include compound (5-1) to compound (5-5). A preferred proportion of the optically active compound is about 5% by weight or less. A further preferred proportion is in the range of about 0.01% by weight to about 2% by weight.

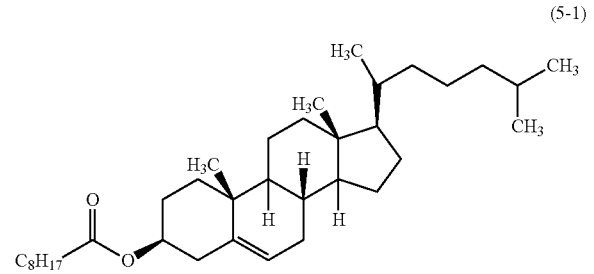

(5-1)

(5-2)

(5-3)

(5-4)

(5-5)

The antioxidant is added to the composition for the purpose of preventing a decrease in the specific resistance caused by heating in air, or maintaining a large voltage holding ratio at room temperature and also at a temperature close to the maximum temperature after the device has been used for a long period of time. Preferred examples of the antioxidant include compound (6) where n is an integer from 1 to 9.

(6)

In compound (6), preferred n is 1, 3, 5, 7 or 9. Further preferred n is 7. Compound (6) where n is 7 is effective in maintaining a large voltage holding ratio at room temperature and also at a temperature close to the maximum temperature after the device has been used for a long period of time because the compound (6) has a small volatility. A preferred proportion of the antioxidant is about 50 ppm or more for achieving the effect thereof, and about 600 ppm or less for avoiding a decrease in the maximum temperature or avoiding an increase in the minimum temperature. A further preferred proportion is in the range of about 100 ppm to about 300 ppm.

Preferred examples of the ultraviolet light absorber include a benzophenone derivative, a benzoate derivative and a triazole derivative. A light stabilizer such as an amine having steric hindrance is also preferred. A preferred proportion of the ultraviolet light absorber or the stabilizer is about 50 ppm or more for achieving the effect thereof, and about 10,000 ppm or less for avoiding a decrease in the maximum temperature or avoiding an increase in the minimum temperature. A further preferred proportion is in the range of about 100 ppm to about 10,000 ppm.

A dichroic dye such as an azo dye and an anthraquinone dye is added to the composition to be adapted to a device having a guest host (GH) mode. A preferred proportion of the dye is in the range of about 0.01% by weight to about 10% by weight. The antifoaming agent such as dimethyl silicone oil or methyl phenyl silicone oil is added to the composition for preventing foam formation. A preferred proportion of the antifoaming agent is about 1 ppm or more for achieving the effect thereof, and about 1,000 ppm or less for avoiding a poor display. A further preferred proportion is in the range of about 1 ppm to about 500 ppm.

The polymerizable compound is used to be adapted to a polymer sustained alignment (PSA) mode device. Compound (4) is suitable for the purpose. A polymerizable compound different from compound (4) may be added to the composition together with compound (4). Preferred examples of the polymerizable compound include a compound such as acrylate, methacrylate, a vinyl compound, a vinyloxy compound, propenyl ether, an epoxy compound (oxirane, oxetane) and vinyl ketone. Further preferred examples include a derivative of acrylate or methacrylate. A preferred proportion of compound (4) is 10% by weight or more based on the total weight of the polymerizable compound. A further preferred proportion is 50% by weight or more. A particularly preferred proportion is 80% by weight or more. A most preferred proportion is 100% by weight.

The polymerizable compound such as compound (4) is polymerized by irradiation with ultraviolet light. The compound may be polymerized in the presence of a suitable initiator such as a photopolymerization initiator. Suitable conditions for polymerization, suitable types of the initiator and suitable amounts thereof are known to those skilled in the art and are described in literatures. For example, Irgacure 651 (registered trademark; BASF), Irgacure 184 (registered trademark; BASF) or Darocur 1173 (registered trademark; BASF), each being a photopolymerization initiator, is suitable for radical polymerization. A preferred proportion of the photopolymerization initiator is in the range of about 0.1% by weight to about 5% by weight based on the total weight of the polymerizable compound. A further preferred proportion is in the range of about 1% by weight to about 3% by weight.

When the polymerizable compound such as compound (4) is stored, the polymerization inhibitor may be added for preventing polymerization. The polymerizable compound is added to the composition ordinarily without removing the polymerization inhibitor. Examples of the polymerization inhibitor include hydroquinone and a hydroquinone derivative such as methylhydroquinone, 4-tert-butylcatechol, 4-methoxyphenol and phenothiazine.

Seventh, the methods for synthesizing the component compounds will be described. The compounds can be prepared according to known methods. Examples of synthetic methods will be shown. Compound (2-1) is prepared according to the method described in JP 2000-053602 A. Compound (3-1) is prepared according to the method described in JP S59-176221 A. Compound (3-13) is prepared according to the method described in JP H2-237949 A. A compound represented by formula (6) where n is 1 is available from Sigma-Aldrich Corporation. Compound (6) where n is 7 and so forth are prepared according to the method described in U.S. Pat. No. 3,660,505 B. Compound (1-1) is prepared according to the method as described below.

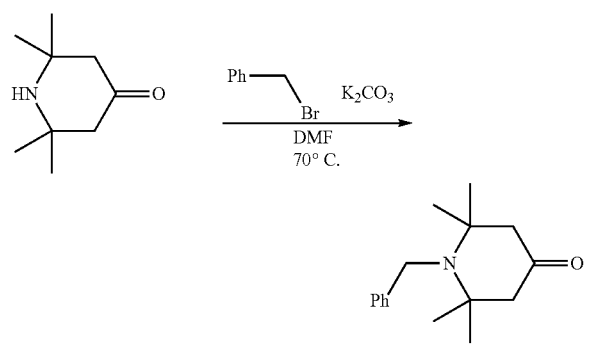

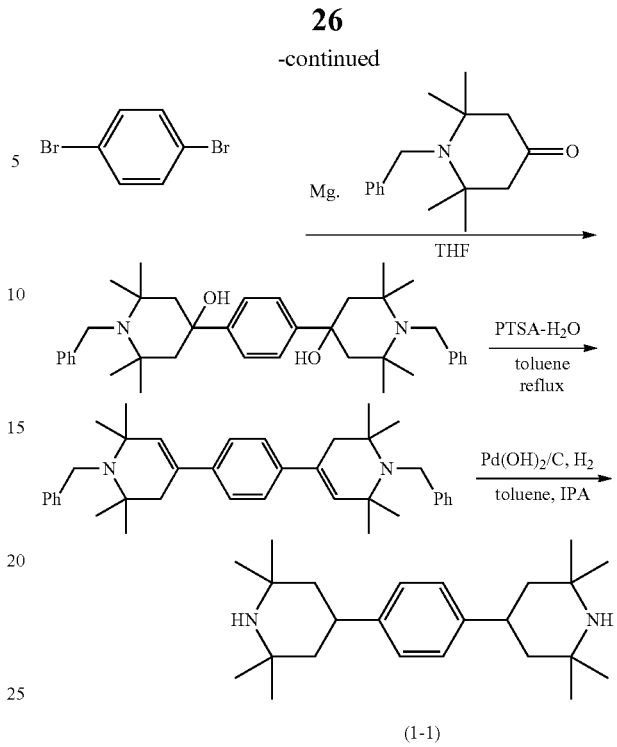

First Step:

A mixture of 2,2,6,6-tetramethylpiperidine-4-one (2.00 g, 12.88 mmol), bromomethylbenzene (2.64 g, 15.43 mmol) and potassium carbonate (3.56 g, 25.77 mmol) was heated and stirred in DMF at 70° C. for 8 hours. The resulting reaction mixture was poured into water and subjected to extraction with toluene. A combined organic layer was washed with a 1 N hydrochloric acid aqueous solution, water and saturated brine, and dried over anhydrous magnesium sulfate. The solvent was distilled off to give 1-benzyl-2,2,6,6-tetramethylpiperidine-4-one (2.53 g, yield 80.1%).

Second Step:

A THF solution of 1,4-dibromobenzene (1.34 g, 5.68 mmol) was slowly added dropwise to a THF suspension of magnesium (0.15 g, 6.25 mmol), while keeping solution temperature at 50° C. or lower. The Grignard reagent obtained was cooled in an ice bath, and a THF solution of 1-benzyl-2,2,6,6-tetramethylpiperidine-4-on (2.53 g, 10.31 mmol) obtained in the first step was slowly added dropwise thereto, while keeping solution temperature at 10° C. or lower. After stirring the reaction mixture at a room temperature for 1 hour, the mixture was quenched in an ammonium chloride aqueous solution, and subjected to extraction with toluene. A combined organic layer was washed with water and saturated brine, and dried over anhydrous magnesium sulfate. A residue was purified by silica gel chromatography to give 4,4'-(1,4-phenylene)bis(l-benzyl-2,2,6,6-tetramethylpiperidine-4-ol) (4.63 g, 7.89 mmol).

Third Step:

In a reactor equipped with a Dean-Stark condenser, 4,4'-(1,4-phenylene)bis(l-benzyl-2,2,6,6-tetramethylpiperidine-4-ol) obtained in the second step (4.63 g, 7.89 mmol), p-toluenesulfonic acid hydrate (0.046 g, 0.24 mmol) and toluene were put, and the resulting mixture was refluxed for 3 hours. The reaction mixture was washed with a saturated aqueous solution of sodium hydrogen carbonate, water and saturation brine, dried over anhydrous magnesium sulfate, and the solvent was distilled off. The residue was purified by silica gel chromatography to give 1,4-bis(1-benzyl-2,2,6,6-tetramethyl-1,2,3,6-tetrahydropyridine-4-yl)benzene (3.62 g, yield 86.1%).

Fourth Step:

The mixture of 1,4-bis(1-benzyl-2,2,6,6-tetramethyl-1,2,3,6-tetrahydropyridine-4-yl)benzene obtained in the third step (3.62 g, 6.79 mmol) and 5% palladium hydroxide/carbon (0.11 g, 3 wt %) was stirred in a mixed solvent of toluene-isopropyl alcohol under a hydrogen atmosphere for 18 hours. The resulting reaction mixture was subjected to filtration and the solvent of the filtrate was distilled off. The residue was purified by silica gel chromatography and recrystallization to give 1,4-bis(2,2,6,6-tetramethylpiperidine-4-yl)benzene (17.2 g, yield 56%).

$^1$H-NMR (CDCl$_3$; δ ppm): 7.17 (s, 4H), 3.00 (tt, 2H), 1.77 (dd, 4H), 1.71-1.59 (br, 1H), 1.31-1.23 (m, 16H), 1.15 (s, 12H), 0.78-0.67 (br, 1H).

Any compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition mainly has a minimum temperature of about −10° C. or lower, a maximum temperature of about 70° C. or higher, and an optical anisotropy in the range of about 0.07 to about 0.20. The device including the composition has a large voltage holding ratio. The composition is suitable for use in the AM device. The composition is particularly suitable for use in a transmissive AM device. The composition having an optical anisotropy in the range of about 0.08 to about 0.25, and also the composition having an optical anisotropy in the range of about 0.10 to about 0.30 may be prepared by controlling the proportion of the component compounds or by mixing with any other liquid crystal compound. The composition can be used as the composition having the nematic phase and as the optically active composition by adding the optically active compound.

The composition can be used for the AM device. The composition can also be used for a PM device. The composition can be used for an AM device and a PM device having a mode such as PC, TN, STN, ECB, OCB, IPS, FFS, VA or FPA. Use for the AM device having the TN, OCB, IPS or FFS mode is particularly preferred. In the AM device having the IPS mode or FFS mode, alignment of liquid crystal molecules in a state in which no voltage is applied may be parallel or may be perpendicular to a glass substrate. The devices may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network-polymer is formed in the composition.

EXAMPLES

The invention will be described in greater detail by way of Examples. The invention is not restricted by the Examples. The invention includes a mixture of the composition in Example 1 and the composition in Example 2. The invention also includes a mixture in which at least two of the compositions in Examples are mixed. A prepared compound was identified by a method such as NMR analysis. Characteristics of compounds and compositions were measured by methods as described below.

NMR analysis: For measurement, DRX-500 (made by Bruker BioSpin Corporation) was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of nuclear magnetic resonance spectra, s, d, t, q, quin, sex, m stand for a singlet, a doublet, a triplet, a quartet, a quintet, a sextet and a multiplet, respectively, and br being broad.

Gas chromatographic analysis: GC-14B Gas Chromatograph made by Shimadzu Corporation was used for measurement. A carrier gas was helium (2 mL per minute). A sample vaporizing chamber and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample vaporizing chamber. A recorder was C-R5A Chromatopac made by Shimadzu Corporation or the equivalent thereof. The resulting chromatogram showed a retention time of a peak and a peak area corresponding to each of the component compounds.

As a solvent for diluting the sample, chloroform, hexane and so forth may also be used. The following capillary columns may also be used for separating the component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A proportion of liquid crystal compounds contained in the composition may be calculated by the method as described below. The mixture of liquid crystal compounds is detected by a gas chromatograph (FID). A ratio of the peak areas in the gas chromatogram corresponds to the ratio (weight ratio) of the liquid crystal compounds. When the capillary columns described above were used, a correction coefficient of each of the liquid crystal compounds may be regarded as 1 (one). Accordingly, the proportion (% by weight) of the liquid crystal compounds can be calculated from the ratio of the peak areas.

Sample for measurement: When characteristics of a composition were measured, the composition was used as was. When the characteristics of a compound were measured, a sample for measurement was prepared by mixing the compound (15% by weight) with a base liquid crystal (85% by weight). Values of characteristics of the compound were calculated using values obtained by measurement, according to an extrapolation method: (extrapolated value)={(measured value of a sample)−0.85×(measured value of base liquid crystal)}/0.15. When a smectic phase (or crystals) precipitated at the ratio thereof at 25° C., a ratio of the compound to the base liquid crystal was changed step by step in the order of (10% by weight: 90% by weight), (5% by weight: 95% by weight) and (1% by weight: 99% by weight). Values of maximum temperature, optical anisotropy, viscosity and dielectric anisotropy with regard to the compound were determined according to the extrapolation method.

The base liquid crystal described below was used. A proportion of the component compounds was expressed in terms of weight percent (% by weight).

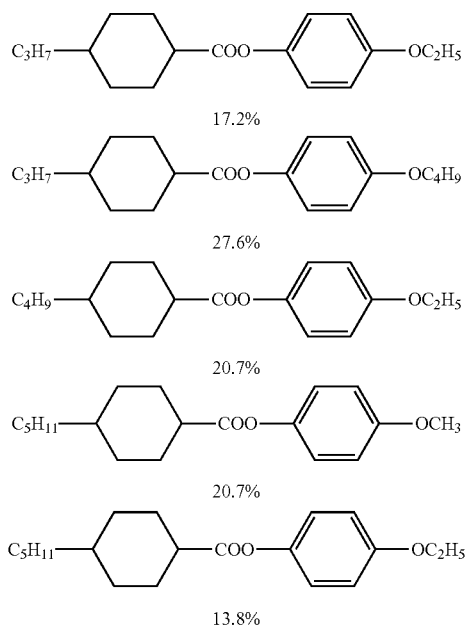

Measuring method: Characteristics were measured according to the methods described below. Most of the measuring methods are applied as described in the Standard of the Japan Electronics and Information Technology Industries Association (hereinafter, abbreviated as JEITA) (JEITA EIAJ ED-2521B) discussed and established by JEITA, or modified thereon. No thin film transistor (TFT) was attached to a TN device used for measurement.

(1) Maximum temperature of nematic phase (NI; ° C.): A sample was placed on a hot plate in a melting point apparatus equipped with a polarizing microscope and was heated at a rate of 1° C. per minute. Temperature when part of the sample began to change from a nematic phase to an isotropic liquid was measured. A maximum temperature of the nematic phase may be occasionally abbreviated as "maximum temperature."

(2) Minimum temperature of nematic phase ($T_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c$<−20° C. A minimum temperature of the nematic phase may be occasionally abbreviated as "minimum temperature."

(3) Viscosity (bulk viscosity; n; measured at 20° C.; mPa·s): A cone-plate (E type) rotational viscometer made by Tokyo Keiki Inc. was used for measurement.

(4) Viscosity (rotational viscosity; yl; measured at 25° C.; mPa·s): Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. A voltage was applied stepwise to the device in the range of 39 V to 50 V at an increment of 1 V. After a period of 0.2 second with no voltage, a voltage was applied repeatedly under the conditions of only one rectangular wave (rectangular pulse; 0.2 second) and no voltage (2 seconds). A peak current and a peak time of a transient current generated by the application were measured. A value of the rotational viscosity was obtained from the measured values and a calculation equation (8) on page 40 of the paper presented by M. Imai et al. Dielectric anisotropy required for the calculation was measured as in section (6).

(5) Optical anisotropy (refractive index anisotropy; An; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(6) Dielectric anisotropy (As; measured at 25° C.): A value of dielectric anisotropy was calculated from an equation: Δn=∈∥−∈⊥. Dielectric constants (∈∥ and ∈⊥) were measured as described below.

(1) Measurement of dielectric constant (∈∥): An ethanol (20 mL) solution of octadecyltriethoxysilane (0.16 mL) was applied to a well-washed glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

(2) Measurement of dielectric constant (∈⊥): A polyimide solution was applied to a well-washed glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(7) Threshold voltage (Vth; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was increased stepwise from 0 V to 20 V at an increment of 0.02 V. On the occasion, the device was irradiated with light from a direction perpendicular to the device, and the amount of light transmitted through the device was measured. A voltage-transmittance curve was prepared, in which the maximum amount of light corresponds to 100% transmittance and the minimum amount of light corresponds to 0% transmittance. A threshold voltage was expressed as a voltage at 10% transmittance.

(8) Voltage holding ratio (VHR-a; measured at 25° C.; %): A PVA device used for measurement had a polyimide alignment film, in which a distance (cell gap) between two glass substrates was 3.5 micrometers. A sample was put in the device, and then the device was sealed with an ultraviolet-curable adhesive. A pulse voltage (60 microseconds at 1 V) was applied to the PVA device and the device was charged. A decaying voltage was measured for 166.7 milliseconds with a high-speed voltmeter, and area A between a voltage curve and a horizontal axis in a unit cycle was obtained. Area B was an area without decay. A voltage holding ratio was expressed as a percentage of area A to area B.

(9) Voltage holding ratio (VHR-b; measured at 60° C.; %): A voltage holding ratio was measured in a manner similar to the procedures except that measurement was carried out at 60° C. The value obtained was expressed in terms of VHR-b.

(10) Voltage holding ratio (VHR-c; measured at 60° C.; %): Stability to ultraviolet light was evaluated by measuring a voltage holding ratio after a device was irradiated with ultraviolet light. A PVA device used for measurement had a polyimide alignment film, in which a distance (cell gap) between two glass substrates was 3.5 micrometers. A sample was injected into the device, and then the device was irradiated with light for 167 minutes. A light source was a black light (peak wavelength 369 nm), and a distance between the device and the light source was 5 millimeters. In VHR-c measurement, a decaying voltage was measured for 166.7 milliseconds. A composition having a large VHR-c has a large stability to ultraviolet light.

(11) Voltage holding ratio (VHR-d; measured at 60° C.; %): A PVA device into which a sample was injected was heated in a constant-temperature bath at 150° C. for 2 hours, and then stability to heat was evaluated by measuring a voltage holding ratio. In VHR-d measurement, a decaying voltage was measured for 166.7 milliseconds. A composition having a large VHR-d has a large stability to heat.

(12) Response time (τ; measured at 25° C.; ms): An LCD-5100 luminance meter made by Otsuka Electronics Co., Ltd. was used for measurement. A light source was a halogen lamp. A low-pass filter was set at 5 kHz. A sample was put in a normally black mode VA device in which a distance (cell gap) between two glass substrates was 4 micrometers and a rubbing direction was anti-parallel. The device was sealed with an ultraviolet-curable adhesive. Rectangular waves (60 Hz, 10 V, 0.5 second) were applied to the device. On the occasion, the device was irradiated with light from a direction perpendicular to the device, and the amount of light transmitted through the device was measured. The maximum amount of light corresponds to 100% transmittance, and the minimum amount of light to 0% transmittance. A response time was expressed in terms of a period of time required for a change from 90% transmittance to 10% transmittance (fall time; millisecond).

(13) Specific resistance (ρ; measured at 25° C.; Ωcm): Into a vessel equipped with electrodes, 1.0 milliliter of a sample was injected. A DC voltage (10 V) was applied to the vessel, and a DC current after 10 seconds was measured. Specific resistance was calculated from the following equation: (specific resistance)={(voltage)×(electric capacity of a vessel)}/{(direct current)×(dielectric constant of vacuum)}.

The compounds described in Examples were expressed using symbols according to definitions in Table 3 below. In Table 3, a configuration of 1,4-cyclohexylene is trans. A parenthesized number next to a symbolized compound corresponds to the number of the compound. A symbol (-) means any other liquid crystal compound. A proportion (percentage) of a liquid crystal compound is expressed in terms of weight percentage (% by weight) based on the weight of the liquid crystal composition. Values of characteristics of the composition were summarized in a last part.

TABLE 3

| Method for Description of Compound using Symbols |
|---|
| R—(A$_1$)—Z$_1$— . . . —Z$_n$—(A$_n$)—R' |

| 1) Left-terminal Group R— | Symbol |
|---|---|
| F—C$_n$H$_{2n}$— | Fn— |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| CH$_2$=CH—COO— | AC— |
| CH$_2$=C(CH$_3$)—COO— | MAC— |

| 2) Right-terminal Group — | Symbol |
|---|---|
| —C$_n$H$_{2n+1}$ | -n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —OCO—CH=CH$_2$ | —AC |
| —OCO—C(CH$_3$)=CH$_2$ | —MAC |

| 3) Bonding Group —Z$_n$— | Symbol |
|---|---|
| —C$_n$H$_{2n}$— | n |
| —COO— | E |
| —CH=CH— | V |
| —CH=CHO— | VO |
| —OCH=CH— | OV |
| —CH$_2$O— | 1O |
| —OCH$_2$— | O1 |

| 4) Ring Structure —A$_n$— | Symbol |
|---|---|
| 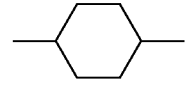 | H |
| 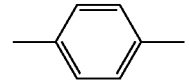 | B |
| 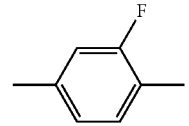 | B(F) |
| 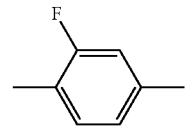 | B(2F) |

TABLE 3-continued

Method for Description of Compound using Symbols
R—(A₁)—Z₁— ... —Zₙ—(Aₙ)—R'

| | |
|---|---|
| 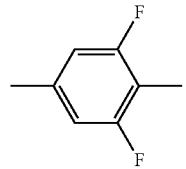 | B(F,F) |
| 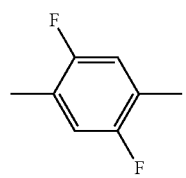 | B(2F,5F) |
| 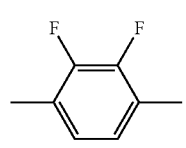 | B(2F,3F) |
| 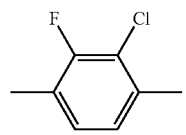 | B(2F,3CL) |
| 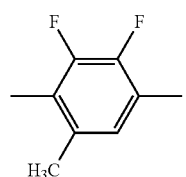 | B(2F,3F,6Me) |
| 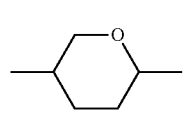 | dh |
| 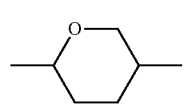 | Dh |
| 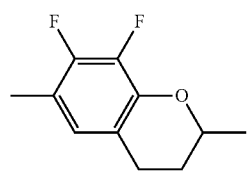 | Cro(7F,8F) |
| 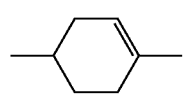 | ch |

5) Examples of Description

Example 1  2-BB(F)B-3

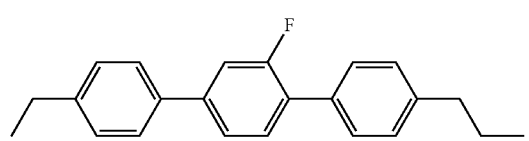 [SMILES: CCCc1ccc(-c2ccc(-c3ccc(CC)cc3)cc2F)cc1]

TABLE 3-continued

Method for Description of Compound using Symbols
R—(A₁)—Z₁— ... —Zₙ—(Aₙ)—R'

Example 2  3-HHB(2F,3F)—O2

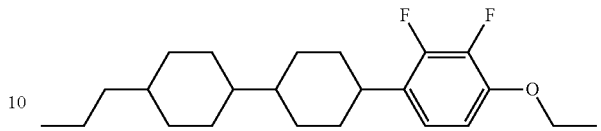

Example 3  V-HHB-1

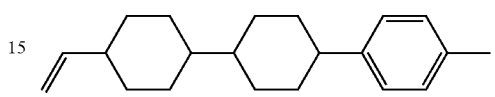

Example 4  3-HDhB(2F,3F)—O2

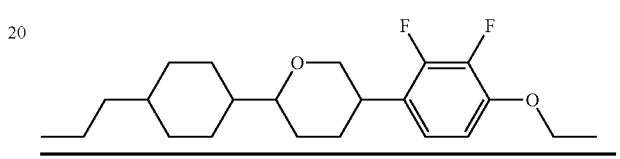

Example 1

| | | |
|---|---|---|
| 2-H1OB(2F,3F)-O2 | (2-3) | 3% |
| 3-H1OB(2F,3F)-O2 | (2-3) | 10% |
| 1V2-BB(2F,3F)-O2 | (2-4) | 10% |
| V-HHB(2F,3F)-O1 | (2-6) | 12% |
| V-HHB(2F,3F)-O2 | (2-6) | 12% |
| 3-HH1OB(2F,3F)-O2 | (2-8) | 6% |
| 2-BB(2F,3F)B-3 | (2-9) | 6% |
| 3-HH-V | (3-1) | 25% |
| 3-HH-V1 | (3-1) | 6% |
| 4-HH-V1 | (3-1) | 3% |
| V-HHB-1 | (3-5) | 3% |
| V2-HHB-1 | (3-5) | 4% |

The composition having a negative dielectric anisotropy described above was prepared and characteristics thereof were measured. NI=80.1° C.; Tc<−20° C.; Δn=0.103; Δ∈=−3.9; Vth=2.09 V; η=20.7 mPa·s.

To the composition, compound (1-3) was added at a ratio of 0.1% by weight and VHR-c was measured. VHR-c=75.4%.

(1-3)

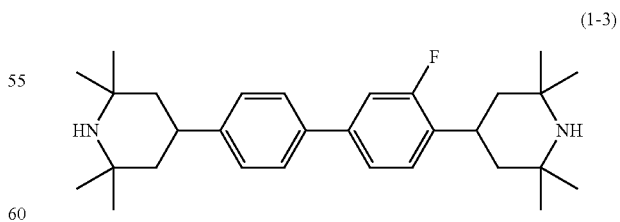

Comparative Example 1

VHR-c of the composition before adding compound (1-3) in Example 1 was measured. VHR-c=35.6%.

Example 2

| | | |
|---|---|---|
| 3-H1OB(2F,3F)-O2 | (2-3) | 8% |
| V2-BB(2F,3F)-O1 | (2-4) | 4% |
| V2-BB(2F,3F)-O2 | (2-4) | 9% |
| 1V2-BB(2F,3F)-O4 | (2-4) | 6% |
| V-HHB(2F,3F)-O2 | (2-6) | 10% |
| V-HHB(2F,3F)-O4 | (2-6) | 3% |
| 1V2-HHB(2F,3F)-O2 | (2-6) | 4% |
| 3-HH1OB(2F,3F)-O2 | (2-8) | 12% |
| 3-HH-V | (3-1) | 26% |
| 1-HH-2V1 | (3-1) | 3% |
| 3-HH-2V1 | (3-1) | 3% |
| 5-HB-O2 | (3-2) | 3% |
| 3-HHB-O1 | (3-5) | 5% |
| V-HHB-1 | (3-5) | 4% |

The composition having a negative dielectric anisotropy described above was prepared and characteristics thereof were measured. NI=77.0° C.; Tc<−20° C.; Δn=0.099; Δ∈=−3.4; Vth=2.22 V; η=18.6 mPa·s. To the composition, compound (1-1) was added at a ratio of 0.05% by weight and VHR-c was measured. VHR-c=68.7%.

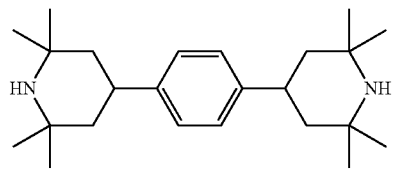

(1-1)

Example 3

| | | |
|---|---|---|
| 3-H2B(2F,3F)-O2 | (2-2) | 15% |
| 5-H2B(2F,3F)-O2 | (2-2) | 12% |
| 3-HHB(2F,3F)-O2 | (2-6) | 8% |
| 5-HHB(2F,3F)-O2 | (2-6) | 6% |
| 2-HHB(2F,3F)-1 | (2-6) | 5% |
| 3-HBB(2F,3F)-O2 | (2-13) | 10% |
| 4-HBB(2F,3F)-O2 | (2-13) | 6% |
| 1V2-HBB(2F,3F)-O2 | (2-13) | 4% |
| 2-HH-3 | (3-1) | 20% |
| 3-HH-4 | (3-1) | 10% |
| V2-BB(F)B-1 | (3-8) | 4% |

The composition having a negative dielectric anisotropy described above was prepared and characteristics thereof were measured. NI=80.0° C.; Tc<−20° C.; Δn=0.096; Δ∈=−3.4; Vth=2.19 V; η=19.0 mPa·s.

To the composition, compound (1-3) was added at a ratio of 0.05% by weight and VHR-c was measured. VHR-c=88.4%.

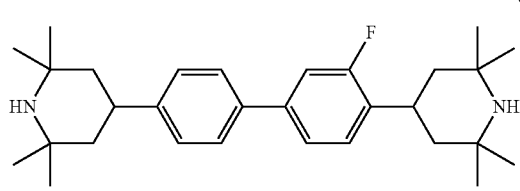

(1-3)

Example 4

| | | |
|---|---|---|
| 3-H1OB(2F,3F)-O2 | (2-3) | 8% |
| 3-BB(2F,3F)-O2 | (2-4) | 8% |
| 2O-BB(2F,3F)-O2 | (2-4) | 5% |
| 2-HH1OB(2F,3F)-O2 | (2-8) | 8% |
| 3-HH1OB(2F,3F)-O2 | (2-8) | 7% |
| 2-BB(2F,3F)B-3 | (2-9) | 8% |
| 3-HDhB(2F,3F)-O2 | (2-11) | 10% |
| 3-HH-V | (3-1) | 24% |
| 3-HH-V1 | (3-1) | 10% |
| V2-HHB-1 | (3-5) | 9% |
| 1O1-HBBH-4 | (-) | 3% |

The composition having a negative dielectric anisotropy described above was prepared and characteristics thereof were measured. NI=83.7° C.; Tc<−20° C.; Δn=0.107; Δ∈=−3.7; Vth=2.21 V; η=22.9 mPa·s.

To the composition, compound (1-1) was added at a ratio of 0.05% by weight and VHR-c was measured. VHR-c=67.5%.

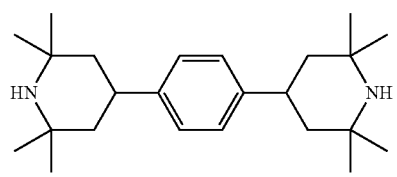

(1-1)

Example 5

| | | |
|---|---|---|
| V2-BB(2F,3F)-O2 | (2-4) | 12% |
| 1V2-BB(2F,3F)-O2 | (2-4) | 5% |
| 1V2-BB(2F,3F)-O4 | (2-4) | 3% |
| V-HHB(2F,3F)-O1 | (2-6) | 5% |
| V-HHB(2F,3F)-O2 | (2-6) | 12% |
| V-HHB(2F,3F)-O4 | (2-6) | 5% |
| 3-HDhB(2F,3F)-O2 | (2-11) | 5% |
| 3-dhBB(2F,3F)-O2 | (2-14) | 4% |
| 3-HH-V | (3-1) | 32% |
| 1-BB-3 | (3-3) | 5% |
| 3-HHEH-3 | (3-4) | 3% |
| V-HHB-1 | (3-5) | 3% |
| 1-BB(F)B-2V | (3-8) | 3% |
| 3-HHEBH-4 | (3-9) | 3% |

The composition having a negative dielectric anisotropy described above was prepared and characteristics thereof were measured. NI=78.6° C.; Tc<−20° C.; Δn=0.107; Δ∈=−2.7; Vth=2.36 V; i=18.8 mPa·s.

To the composition, compound (1-3) was added at a ratio of 0.07% by weight and VHR-c was measured. VHR-c=73.6%.

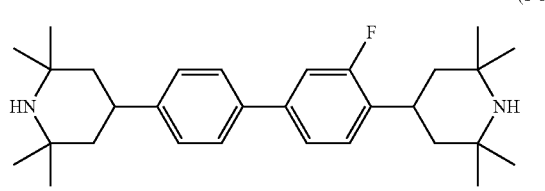

(1-3)

Example 6

| | | |
|---|---|---|
| V2-BB(2F,3F)-O2 | (2-4) | 12% |
| 1V2-BB(2F,3F)-O2 | (2-4) | 6% |
| 1V2-BB(2F,3F)-O4 | (2-4) | 3% |
| V-HHB(2F,3F)-O1 | (2-6) | 6% |
| V-HHB(2F,3F)-O2 | (2-6) | 7% |
| V-HHB(2F,3F)-O4 | (2-6) | 5% |
| 1V2-HHB(2F,3F)-O4 | (2-6) | 5% |
| 3-DhH1OB(2F,3F)-O2 | (2-12) | 5% |
| 3-dhBB(2F,3F)-O2 | (2-14) | 5% |
| 3-HH-V | (3-1) | 26% |
| 3-HH-VFF | (3-1) | 3% |
| V2-HB-1 | (3-2) | 6% |
| V-HHB-1 | (3-5) | 5% |
| 2-BB(F)B-5 | (3-8) | 3% |
| 5-HBB(F)B-3 | (3-13) | 3% |

The composition having a negative dielectric anisotropy described above was prepared and characteristics thereof were measured. NI=79.0° C.; Tc<-20° C.; Δn=0.112; Δ∈=-2.9; Vth=2.35 V; η=19.8 mPa·s.

To the composition, compound (1-1) was added at a ratio of 0.1% by weight and VHR-c was measured. VHR-c=74.7%.

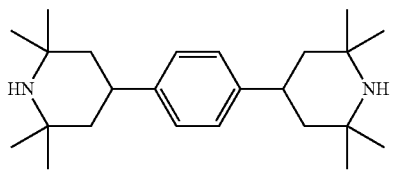

(1-1)

Example 7

| | | |
|---|---|---|
| 3-H1OB(2F,3F)-O2 | (2-3) | 10% |
| 1V2-BB(2F,3F)-O2 | (2-4) | 10% |
| V-HHB(2F,3F)-O1 | (2-6) | 11% |
| V-HHB(2F,3F)-O2 | (2-6) | 12% |
| 3-HH1OB(2F,3F)-O2 | (2-8) | 9% |
| 2-BB(2F,3F)B-3 | (2-9) | 7% |
| 3-HH-V | (3-1) | 26% |
| 3-HH-V1 | (3-1) | 6% |
| 1-HH-2V1 | (3-1) | 3% |
| 3-HHB-3 | (3-5) | 3% |
| V-HHB-1 | (3-5) | 3% |

The composition having a negative dielectric anisotropy described above was prepared and characteristics thereof were measured. NI=81.6° C.; Tc<-20° C.; Δn=0.103; Δ∈=-3.7; Vth=2.15 V; η=20.9 mPa·s.

To the composition, compound (1-1) was added at a ratio of 0.06% by weight and VHR-c was measured. VHR-c=66.7%.

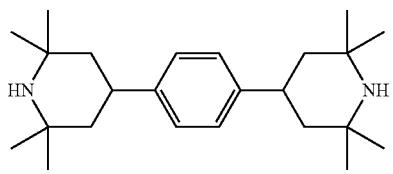

(1-1)

Example 8

| | | |
|---|---|---|
| 3-HB(2F,3F)-O2 | (2-1) | 8% |
| 3-H1OB(2F,3F)-O2 | (2-3) | 8% |
| 3-BB(2F,3F)-O2 | (2-4) | 5% |
| 2-HH1OB(2F,3F)-O2 | (2-8) | 8% |
| 3-HH1OB(2F,3F)-O2 | (2-8) | 7% |
| 3-HDhB(2F,3F)-O2 | (2-11) | 10% |
| 3-HH-V | (3-1) | 25% |
| 3-HH-V1 | (3-1) | 10% |
| V2-HHB-1 | (3-5) | 11% |
| 2-BB(F)B-3 | (3-8) | 8% |

The composition having a negative dielectric anisotropy described above was prepared and characteristics thereof were measured. NI=79.4° C.; Tc<-20° C.; Δn=0.100; Δ∈=-3.5; Vth=2.20 V; η=19.5 mPa·s.

To the composition, compound (1-3) was added at a ratio of 0.05% by weight and VHR-c was measured. VHR-c=76.3%.

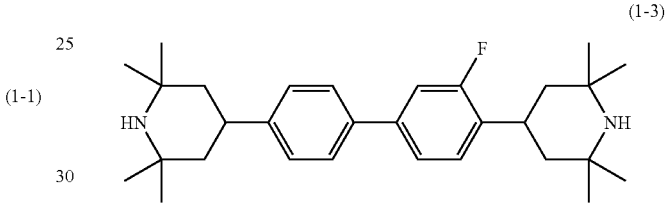

(1-3)

Example 9

| | | |
|---|---|---|
| V2-HB(2F,3F)-O2 | (2-1) | 5% |
| 3-H2B(2F,3F)-O2 | (2-2) | 9% |
| 3-HHB(2F,3F)-O2 | (2-6) | 12% |
| 2-HH1OB(2F,3F)-O2 | (2-8) | 7% |
| 3-HH1OB(2F,3F)-O2 | (2-8) | 12% |
| 3-HDhB(2F,3F)-O2 | (2-11) | 3% |
| 2-HH-3 | (3-1) | 27% |
| 1-BB-3 | (3-3) | 13% |
| 3-HHB-1 | (3-5) | 3% |
| 3-B(F)BB-2 | (3-7) | 3% |
| 3-HB(F)HH-5 | (3-10) | 3% |
| 3-HB(F)BH-3 | (3-12) | 3% |

The composition having a negative dielectric anisotropy described above was prepared and characteristics thereof were measured. NI=78.9° C.; Tc<-20° C.; Δn=0.098; Δ∈=-2.9; Vth=2.34 V; η=18.2 mPa·s.

To the composition, compound (1-3) was added at a ratio of 0.03% by weight and VHR-c was measured. VHR-c=76.2%.

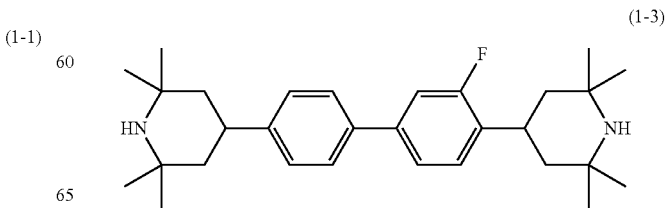

(1-3)

Example 10

| | | |
|---|---|---|
| 5-H2B(2F,3F)-O2 | (2-2) | 9% |
| 5-BB(2F,3F)-O4 | (2-4) | 5% |
| 5-HHB(2F,3F)-O2 | (2-6) | 3% |
| V-HHB(2F,3F)-O2 | (2-6) | 6% |
| 3-HH2B(2F,3F)-O2 | (2-7) | 3% |
| 3-HH1OB(2F,3F)-O2 | (2-8) | 13% |
| 2-BB(2F,3F)B-3 | (2-9) | 3% |
| 2-HHB(2F,3CL)-O2 | (2-16) | 3% |
| 4-HHB(2F,3CL)-O2 | (2-16) | 3% |
| 2-HH-3 | (3-1) | 22% |
| 3-HH-V | (3-1) | 5% |
| V2-BB-1 | (3-3) | 3% |
| 1-BB-3 | (3-3) | 13% |
| 3-HB(F)HH-5 | (3-10) | 3% |
| 5-HBBH-3 | (3-11) | 3% |
| 3-HB(F)BH-3 | (3-12) | 3% |

The composition having a negative dielectric anisotropy described above was prepared and characteristics thereof were measured. NI=78.9° C.; Tc<−20° C.; Δn=0.103; Δ∈= −2.6; Vth=2.49 V; η=17.6 mPa·s.

To the composition, compound (1-1) was added at a ratio of 0.05% by weight and VHR-c was measured. VHR-c=73.4%.

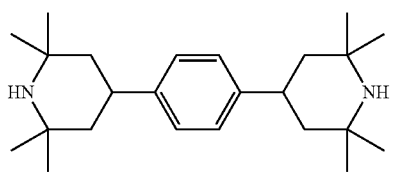
(1-1)

Example 11

| | | |
|---|---|---|
| 3-H2B(2F,3F)-O2 | (2-2) | 20% |
| 5-H2B(2F,3F)-O2 | (2-2) | 12% |
| 3-HHB(2F,3F)-O2 | (2-6) | 8% |
| 5-HHB(2F,3F)-O2 | (2-6) | 6% |
| 3-HDhB(2F,3F)-O2 | (2-11) | 5% |
| 3-HBB(2F,3F)-O2 | (2-13) | 10% |
| 4-HBB(2F,3F)-O2 | (2-13) | 6% |
| 2-HH-3 | (3-1) | 16% |
| 3-HH-4 | (3-1) | 13% |
| 1V-HBB-2 | (3-6) | 4% |

The composition having a negative dielectric anisotropy described above was prepared and characteristics thereof were measured. NI=76.2° C.; Tc<−20° C.; Δn=0.089; Δ∈= −3.6; Vth=2.12 V; η=19.8 mPa·s.

To the composition, compound (1-3) was added at a ratio of 0.03% by weight and VHR-c was measured. VHR-c=89.1%.

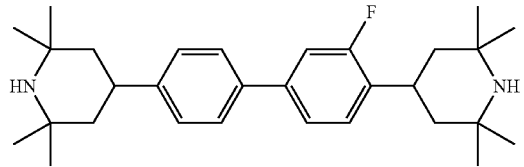
(1-3)

Example 12

| | | |
|---|---|---|
| 3-HB(2F,3F)-O2 | (2-1) | 5% |
| V-HB(2F,3F)-O4 | (2-1) | 4% |
| 5-BB(2F,3F)-O2 | (2-4) | 6% |
| 3-B(2F,3F)B(2F,3F)-O2 | (2-5) | 3% |
| V-HHB(2F,3F)-O2 | (2-6) | 10% |
| 3-HH1OB(2F,3F)-O2 | (2-8) | 10% |
| 2-BB(2F,3F)B-3 | (2-9) | 5% |
| 4-HBB(2F,3F)-O2 | (2-13) | 5% |
| V-HBB(2F,3F)-O2 | (2-13) | 7% |
| 3-HBB(2F,3CL)-O2 | (2-17) | 3% |
| 3-HH-O1 | (3-1) | 3% |
| 3-HH-V | (3-1) | 26% |
| 3-HB-O2 | (3-2) | 3% |
| V-HHB-1 | (3-5) | 7% |
| 3-BB(F)B-5 | (3-8) | 3% |

The composition having a negative dielectric anisotropy described above was prepared and characteristics thereof were measured. NI=80.6° C.; Tc<−20° C.; Δn=0.114; Δ∈= −3.2; Vth=2.27 V; η=24.0 mPa·s.

To the composition, (1-1) was added at a ratio of 0.1% by weight and VHR-c was measured. VHR-c=65.9%.

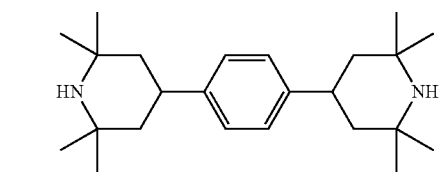
(1-1)

Example 13

| | | |
|---|---|---|
| 3-BB(2F,3F)-O4 | (2-4) | 6% |
| V2-BB(2F,3F)-O2 | (2-4) | 12% |
| 3-HHB(2F,3F)-O2 | (2-6) | 5% |
| V-HHB(2F,3F)-O1 | (2-6) | 6% |
| V-HHB(2F,3F)-O2 | (2-6) | 12% |
| 3-DhHB(2F,3F)-O2 | (2-10) | 5% |
| 3-HB(2F,3F)B(2F,3F)-O2 | (2-15) | 3% |
| 3-H1OCro(7F,8F)-5 | (2-18) | 3% |
| 3-HH1OCro(7F,8F)-5 | (2-19) | 3% |
| 3-HH-V | (3-1) | 23% |
| 4-HH-V | (3-1) | 3% |
| 5-HH-V | (3-1) | 6% |
| 7-HB-1 | (3-2) | 3% |
| V-HHB-1 | (3-5) | 4% |
| V-HBB-2 | (3-6) | 3% |
| 2-BB(F)B-3 | (3-8) | 3% |

The composition having a negative dielectric anisotropy described above was prepared and characteristics thereof were measured. NI=74.9° C.; Tc<-20° C.; Δn=0.099; Δ∈= -3.1; Vth=2.21 V; η=23.4 mPa·s.

To the composition, compound (1-3) was added at a ratio of 0.2% by weight and VHR-c was measured. VHR-c=79.6%.

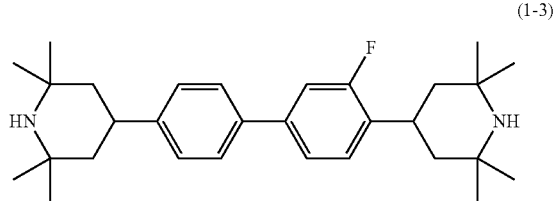

(1-3)

Example 14

| | | |
|---|---|---|
| 3-BB(2F,3F)-O4 | (2-4) | 6% |
| V2-BB(2F,3F)-O2 | (2-4) | 12% |
| 3-HHB(2F,3F)-O2 | (2-6) | 5% |
| V-HHB(2F,3F)-O1 | (2-6) | 6% |
| V2-HHB(2F,3F)-O2 | (2-6) | 12% |
| 3-DhHB(2F,3F)-O2 | (2-10) | 5% |
| 3-HEB(2F,3F)B(2F,3F)-O2 | (2-15) | 3% |
| 3-H1OCro(7F,8F)-5 | (2-18) | 3% |
| 3-HH1OCro(7F,8F)-5 | (2-19) | 3% |
| 3-HH-V | (3-1) | 23% |
| 4-HH-V | (3-1) | 3% |
| 5-HH-V | (3-1) | 6% |
| 7-HB-1 | (3-2) | 3% |
| V-HHB-1 | (3-5) | 4% |
| V-HBB-2 | (3-6) | 3% |
| 2-BB(F)B-3 | (3-8) | 3% |

The composition having a negative dielectric anisotropy described above was prepared and characteristics thereof were measured. NI=76.1° C.; Tc<-20° C.; Δn=0.099; Δ∈= -3.0; Vth=2.25 V; η=22.7 mPa·s.

To the composition, compound (1-2) was added at a ratio of 0.15% by weight and VHR-c was measured. VHR-c=77.2%.

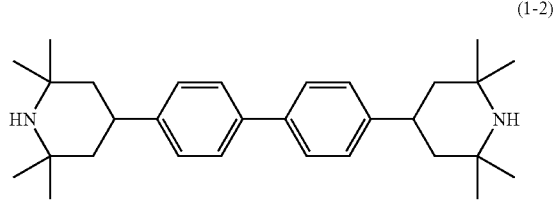

(1-2)

Example 15

| | | |
|---|---|---|
| 3-H2B(2F,3F)-O2 | (2-2) | 20% |
| 5-H2B(2F,3F)-O2 | (2-2) | 12% |
| 3-HHB(2F,3F)-O2 | (2-6) | 8% |
| 5-HHB(2F,3F)-O2 | (2-6) | 6% |
| 3-HDhB(2F,3F)-O2 | (2-11) | 5% |
| 3-HBB(2F,3F)-O2 | (2-13) | 10% |
| 4-HBB(2F,3F)-O2 | (2-13) | 6% |
| 2-HH-3 | (3-1) | 16% |
| 3-HH-4 | (3-1) | 13% |
| V-HBB-2 | (3-6) | 4% |

The composition having a negative dielectric anisotropy described above was prepared and characteristics thereof were measured. NI=75.6° C.; Tc<-20° C.; Δn=0.089; Δ∈=-3.6; Vth=2.11 V; η=19.5 mPa·s.

To the composition, compound (1) was added at a ratio of 0.03% by weight and VHR-c was measured. VHR-c=87.5%.

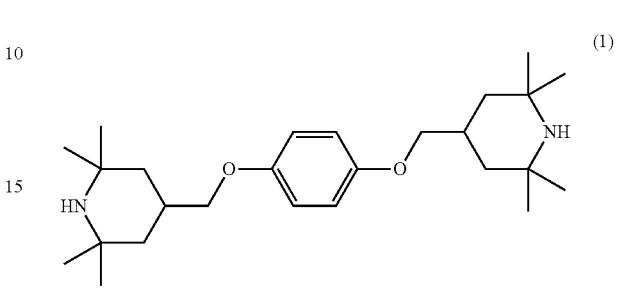

(1)

The compositions in Example 1 to Example 15 were found to have a larger voltage holding ratio after irradiation with ultraviolet light in comparison with the composition in Comparative Example 1. Therefore, the liquid crystal composition of the invention can be concluded to have excellent characteristics.

INDUSTRIAL APPLICABILITY

A liquid crystal composition of the invention satisfies at least one of characteristics such as a high maximum temperature, a low minimum temperature, a small viscosity, a suitable optical anisotropy, a large negative dielectric anisotropy, a large specific resistance, a high stability to ultraviolet light and a high stability to heat, or has a suitable balance regarding at least two of the characteristics. A liquid crystal display device including the composition has characteristics such as a short response time, a large voltage holding ratio, a low threshold voltage, a large contrast ratio and a long service life, and therefore can be used for a liquid crystal projector, a liquid crystal television and so forth.

What is claimed is:

1. A liquid crystal composition that has a negative dielectric anisotropy and a nematic phase, and contains at least one compound selected from the group of compounds represented by formula (1-1) to formula (1-3):

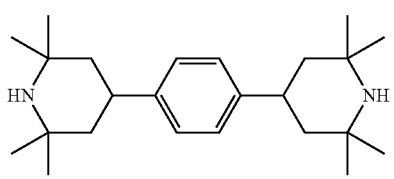

(1-1)

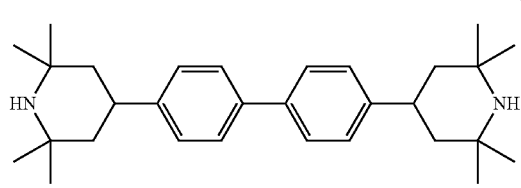

(1-2)

(1-3)

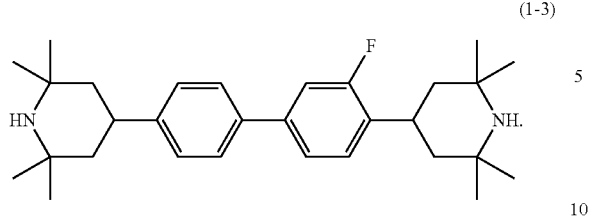

2. The liquid crystal composition according to claim 1, wherein a proportion of a compound represented by formula (1) is in the range of 0.005% by weight to 1% by weight based on the weight of the liquid crystal composition.

3. The liquid crystal composition according to claim 1, containing at least one compound represented by formula (2) as a first component:

(2)

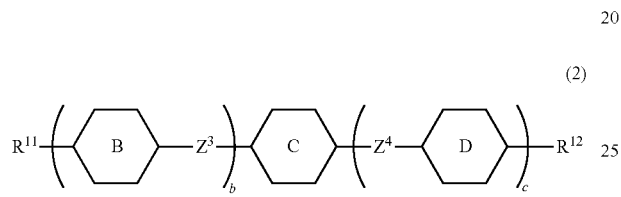

wherein, in formula (2), $R^{11}$ and $R^{12}$ are independently alkyl having 1 to 12 carbons, alkoxy having 1 to 12 carbons, alkenyl having 2 to 12 carbons or alkenyloxy having 2 to 12 carbons; ring B and ring D are independently 1,4-cyclohexylene, 1,4-cyclohexenylene, 1,4-phenylene, 1,4-phenylene in which at least one hydrogen is replaced by fluorine or chlorine, or tetrahydropyran-2,5-diyl; ring C is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^3$ and $Z^4$ are independently a single bond, ethylene, methyleneoxy or carbonyloxy; b is 1, 2 or 3 and c is 0 or 1; and a sum of b and c is 3 or less.

4. The liquid crystal composition according to claim 3, containing at least one compound selected from the group of compounds represented by formula (2-1) to formula (2-19) as the first component:

(2-1)

(2-2)

(2-3)
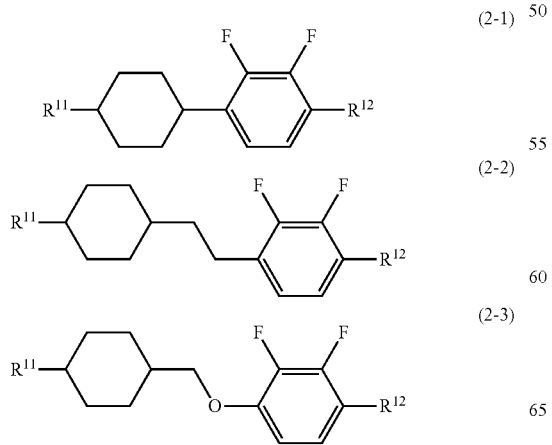

(2-4)

(2-5)

(2-6)
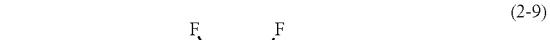

(2-7)

(2-8)

(2-9)

(2-10)

(2-11)

(2-12)

(2-13)

(2-14)
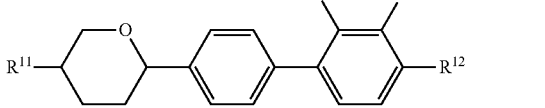

-continued (2-15)
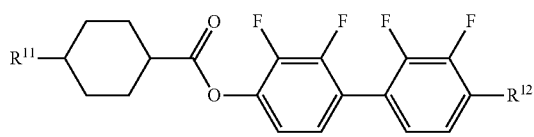

(2-16)
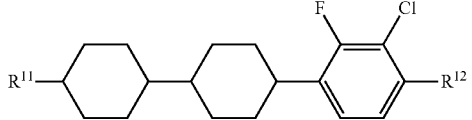

(2-17)
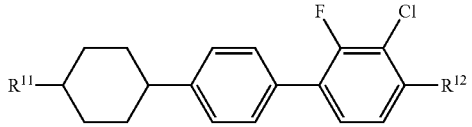

(2-18)
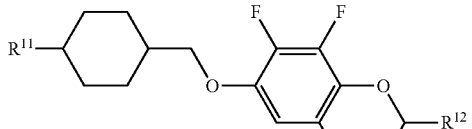

(2-19)
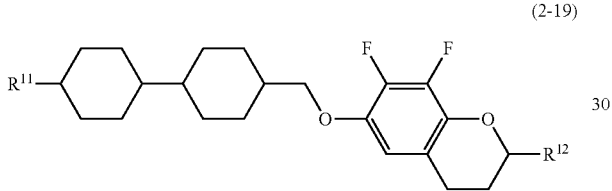

wherein, in formula (2-1) to formula (2-19), $R^{11}$ and $R^{12}$ are independently alkyl having 1 to 12 carbons, alkoxy having 1 to 12 carbons, alkenyl having 2 to 12 carbons or alkenyloxy having 2 to 12 carbons.

5. The liquid crystal composition according to claim 3, wherein a proportion of the first component is in the range of 10% by weight to 90% by weight based on the weight of the liquid crystal composition.

6. The liquid crystal composition according to claim 1, containing at least one compound represented by formula (3) as a second component:

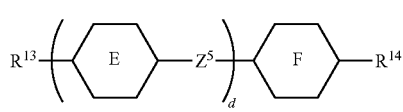
(3)

wherein, in formula (3), $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine; ring E and ring F are independently 1,4-cyclohexylene, 1,4-phenylene, 2-fluoro-1,4-phenylene or 2,5-difluoro-1,4-phenylene; $Z^5$ is a single bond, ethylene or carbonyloxy; and d is 1, 2 or 3.

7. The liquid crystal composition according to claim 6, containing at least one compound selected from the group of compounds represented by formula (3-1) to formula (3-13) as the second component:

(3-1)
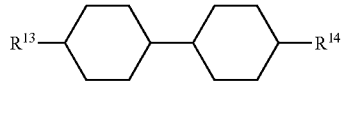

(3-2)
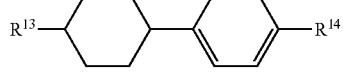

(3-3)
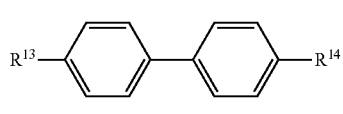

(3-4)
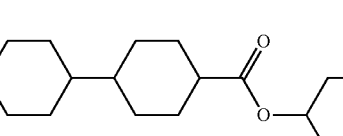

(3-5)
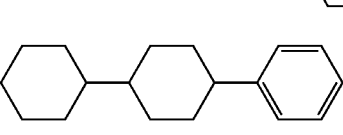

(3-6)
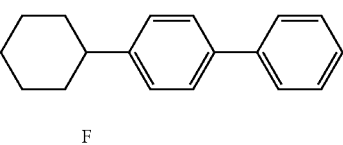

(3-7)
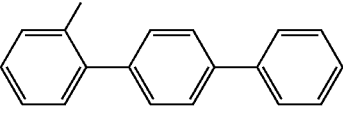

(3-8)
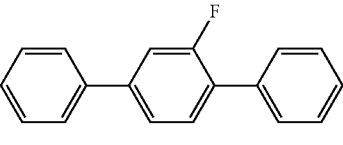

(3-9)
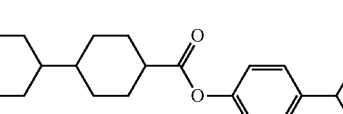

(3-10)
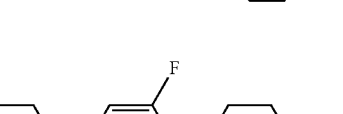

(3-11)
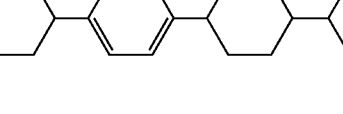

(3-12)
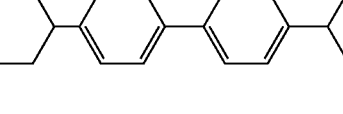

-continued (3-13)

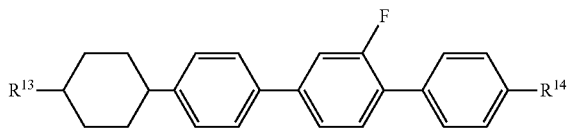

wherein, in formula (3-1) to formula (3-13), $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine.

8. The liquid crystal composition according to claim 6, wherein a proportion of the second component is in the range of 10% by weight to 90% by weight based on the weight of the liquid crystal composition.

9. The liquid crystal composition according to claim 1, containing at least one polymerizable compound represented by formula (4):

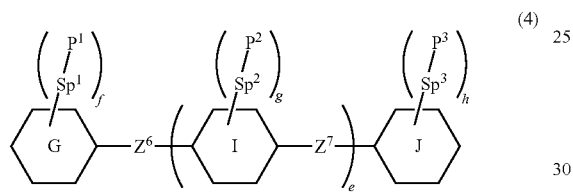

(4)

wherein, in formula (4), ring G and ring J are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen; ring I is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen; $Z^6$ and $Z^7$ are independently a single bond or alkylene having 1 to 10 carbons, and in the alkylene, at least one —CH$_2$— may be replaced by —O—, —CO—, —COO— or —OCO—, at least one —CH$_2$—CH$_2$— may be replaced by —CH═CH—, —C(CH$_3$)═CH—, —CH═C(CH$_3$)— or —C(CH$_3$)═C(CH$_3$)—, and in the groups, at least one hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one —CH$_2$— may be replaced by —O—, —COO—, —OCO— or —OCOO—, at least one —CH$_2$—CH$_2$— may be replaced by —CH═CH— or —C≡C—, and in the groups, at least one hydrogen may be replaced by fluorine or chlorine; e is 0, 1 or 2; f, g and h are independently 0, 1, 2, 3 or 4; and a sum of f, g and h is 1 or more.

10. The liquid crystal composition according to claim 9, wherein, in formula (4) described in claim 9, $P^1$, $P^2$ and $P^3$ are independently a polymerizable group selected from the group of groups represented by formula (P-1) to formula (P-6):

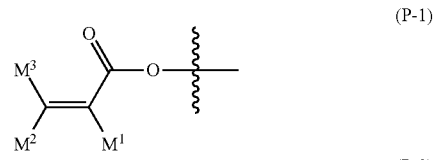

(P-1)

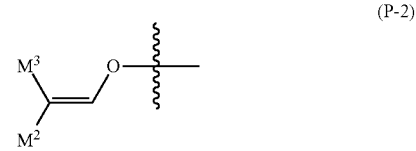

(P-2)

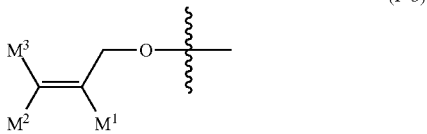

(P-3)

(P-4)

(P-5)

(P-6)

wherein, in formula (P-1) to formula (P-6), $M^1$, $M^2$ and $M^3$ are independently hydrogen, fluorine, alkyl having 1 to 5 carbons, or alkyl having 1 to 5 carbons in which at least one hydrogen is replaced by halogen; and when both of $P^1$ and $P^3$ are a group represented by formula (P-4), at least one of $Sp^1$ and $Sp^3$ is alkylene in which at least one —CH$_2$— is replaced by —O—, —COO—, —OCO— or —OCOO—.

11. The liquid crystal composition according to claim 9, containing at least one polymerizable compound selected from the group of compounds represented by formula (4-1) to formula (4-27):

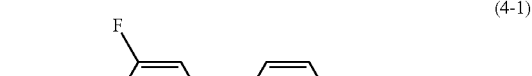

(4-1)

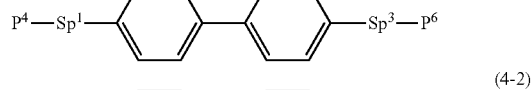

(4-2)

(4-3) 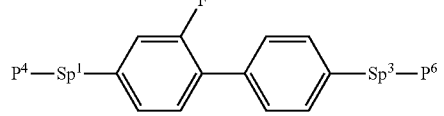
(4-4) 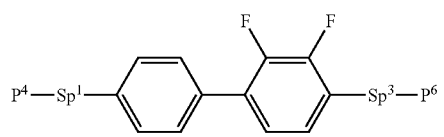
(4-5) 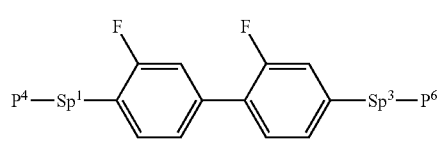
(4-6) 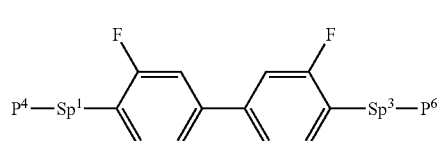
(4-7) 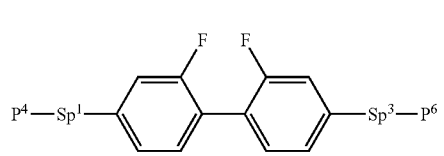
(4-8) 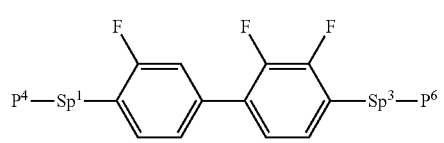
(4-9) 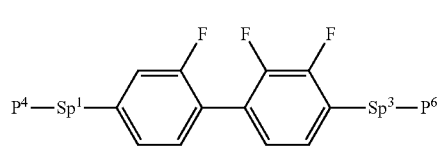
(4-10) 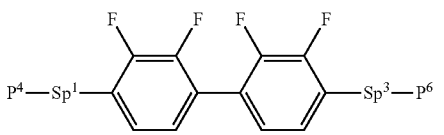
(4-11) 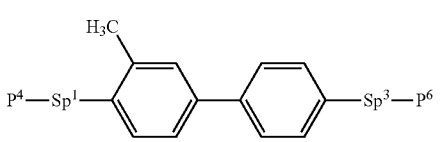
(4-12) 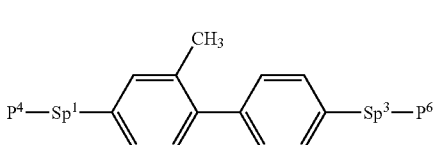
(4-13) 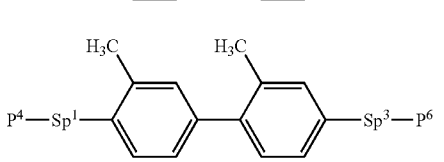
(4-14) 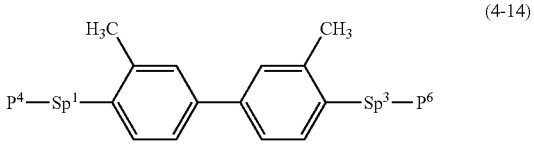
(4-15) 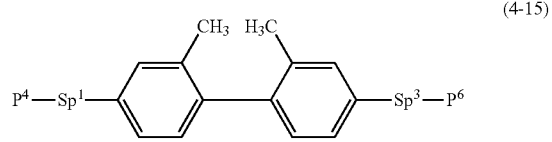
(4-16) 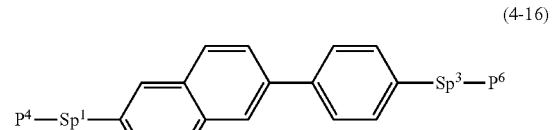
(4-17) 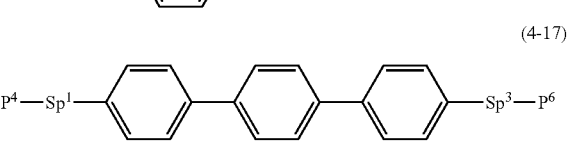
(4-18) 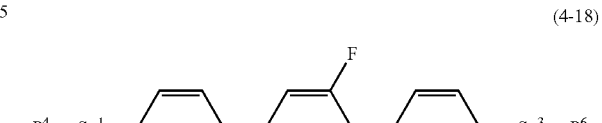
(4-19) 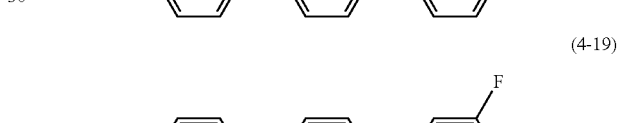
(4-20) 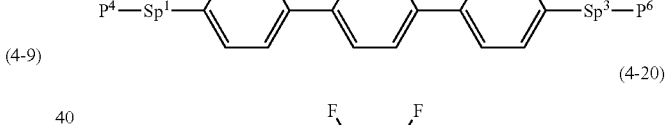
(4-21) 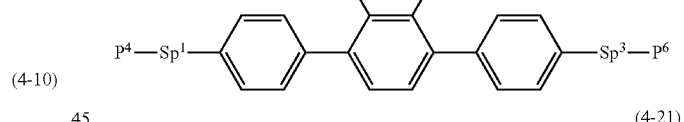
(4-22) 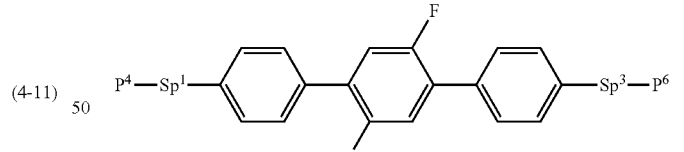
(4-23) 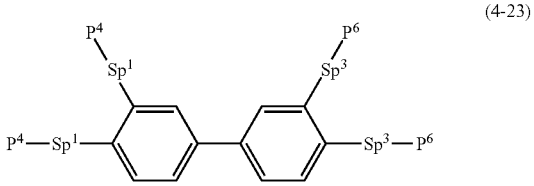

-continued

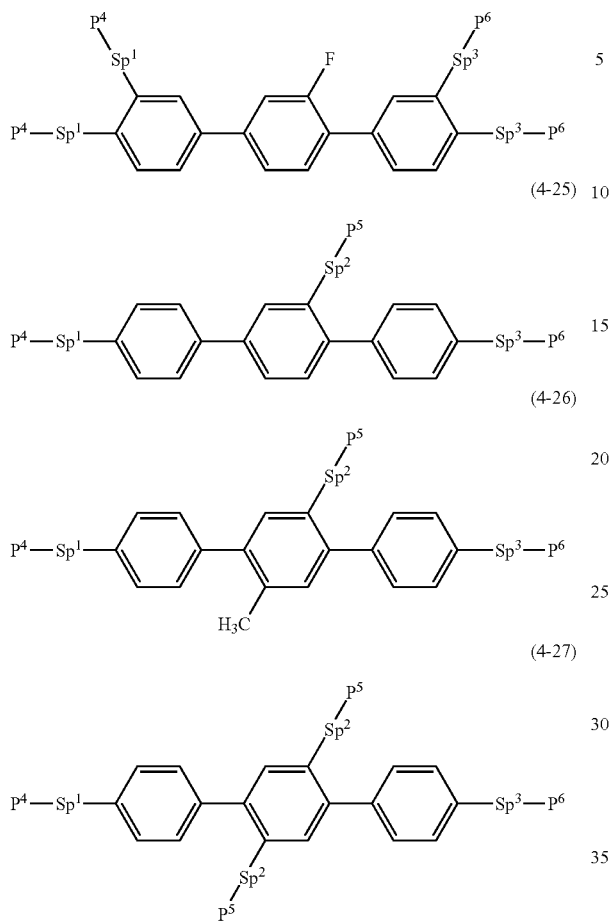

wherein, in formula (4-1) to formula (4-27), $P^4$, $P^5$ and $P^6$ are independently a polymerizable group selected from the group of groups represented by formula (P-1) to formula (P-3);

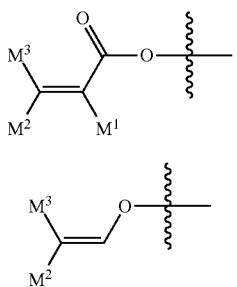

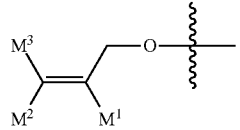

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one hydrogen is replaced by halogen; $Sp^1$, $Sp^2$ and $Sp^a$ are independently a single bond or alkylene having 1 to 10 carbons, and in the alkylene, at least one —$CH_2$— may be replaced by —O—, —COO—, —OCO— or —OCOO—, at least one —$CH_2$—$CH_2$— may be replaced by —CH=CH— or —C≡C—, and in the groups, at least one hydrogen may be replaced by fluorine or chlorine.

12. The liquid crystal composition according to claim 9, wherein a proportion of a compound represented by formula (4) is in the range of 0.03% by weight to 10% by weight based on the weight of the liquid crystal composition.

13. A liquid crystal display device, including the liquid crystal composition according to claim 1.

14. The liquid crystal display device according to claim 13, wherein an operating mode in the liquid crystal display device is an IPS mode, a VA mode, an FFS mode or an FPA mode, and a driving mode in the liquid crystal display device is an active matrix mode.

15. A polymer sustained alignment mode liquid crystal display device, wherein the device includes the liquid crystal composition according to claim 9, and a polymerizable compound in the liquid crystal composition is polymerized.

16. The liquid crystal composition according to claim 3, containing at least one compound represented by formula (3) as a second component:

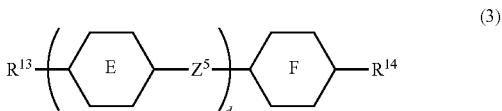

wherein, in formula (3), $R^{13}$ and $R^{14}$ are independently alkyl having 1 to 12 carbons, alkoxy having 1 to 12 carbons, alkenyl having 2 to 12 carbons, or alkenyl having 2 to 12 carbons in which at least one hydrogen is replaced by fluorine; ring E and ring F are independently 1,4-cyclohexylene, 1,4-phenylene, 2-fluoro-1,4-phenylene or 2,5-difluoro-1,4-phenylene; $Z^5$ is a single bond, ethylene or carbonyloxy; and d is 1, 2 or 3.

\* \* \* \* \*

UNITED STATES PATENT AND TRADEMARK OFFICE
CERTIFICATE OF CORRECTION

PATENT NO. : 9,969,935 B2
APPLICATION NO. : 15/038739
DATED : May 15, 2018
INVENTOR(S) : Yoshimasa Furusato et al.

Page 1 of 1

It is certified that error appears in the above-identified patent and that said Letters Patent is hereby corrected as shown below:

On the Title Page

Item (87) "PCT Pub. Date: Apr. 6, 2015" should be changed to -- PCT Pub. Date: June 4, 2015 --.

Signed and Sealed this
Tenth Day of July, 2018

Andrei Iancu
*Director of the United States Patent and Trademark Office*